US012599708B2

(12) United States Patent
Vp et al.

(10) Patent No.: US 12,599,708 B2
(45) Date of Patent: Apr. 14, 2026

(54) PERITONEAL DIALYSIS CASSETTE

(71) Applicant: MOZARC MEDICAL US LLC, Minneapolis, MN (US)

(72) Inventors: Rajkumar Vp, Dindigul (IN); Rathnakara Narayana, Bangalore (IN); Vikas Chitradurga Mruthyunjaya, Chitradurga (IN)

(73) Assignee: Mozarc Medical US LLC, Minneapolis, MN (US)

( * ) Notice: Subject to any disclaimer, the term of this patent is extended or adjusted under 35 U.S.C. 154(b) by 1274 days.

(21) Appl. No.: 17/406,848

(22) Filed: Aug. 19, 2021

(65) Prior Publication Data
US 2023/0054072 A1 Feb. 23, 2023

(51) Int. Cl.
*A61M 1/14* (2006.01)
*A61M 1/28* (2006.01)

(52) U.S. Cl.
CPC .......... *A61M 1/159* (2022.05); *A61M 1/1524* (2022.05); *A61M 1/154* (2022.05); *A61M 1/1561* (2022.05); *A61M 1/28* (2013.01); *A61M 2205/12* (2013.01); *A61M 2205/121* (2013.01); *A61M 2205/127* (2013.01); *A61M 2205/3331* (2013.01); *A61M 2205/3368* (2013.01); *A61M 2210/1017* (2013.01)

(58) Field of Classification Search
CPC ...... A61M 1/15; A61M 1/152; A61M 1/1524; A61M 1/154; A61M 1/156; A61M 1/1561; A61M 1/159; A61M 1/28; A61M 2205/12; A61M 2205/121; A61M 2205/33; A61M 2205/3327; A61M 2205/3331; A61M 2205/3368; A61M 2205/50; A61M 2210/1017; A61M 1/14; A61M 5/16813
See application file for complete search history.

(56) References Cited

U.S. PATENT DOCUMENTS

| | | | | |
|---|---|---|---|---|
| 5,273,517 A | * | 12/1993 | Barone | A61M 1/36226 |
| | | | | 417/474 |
| 8,784,359 B2 | | 7/2014 | Plahey et al. | |
| 9,028,440 B2 | * | 5/2015 | Helmore | G16H 20/40 |
| | | | | 604/27 |

* cited by examiner

*Primary Examiner* — Shefali D Patel

(57) ABSTRACT

An example article includes a rigid member defining a plurality of fluid flow paths and a plurality of flexible tubes each defining a lumen and configured to be occluded via a pressure applied externally to the lumen and unoccluded in an absence of the externally applied pressure. Each flexible tube of the plurality of flexible tubes is configured to be fluidically connected to a flow path of the plurality of flow paths, and different fluid flow paths of the plurality of fluid flow paths are defined by occluding different flexible tubes of the plurality of flexible tubes.

20 Claims, 12 Drawing Sheets

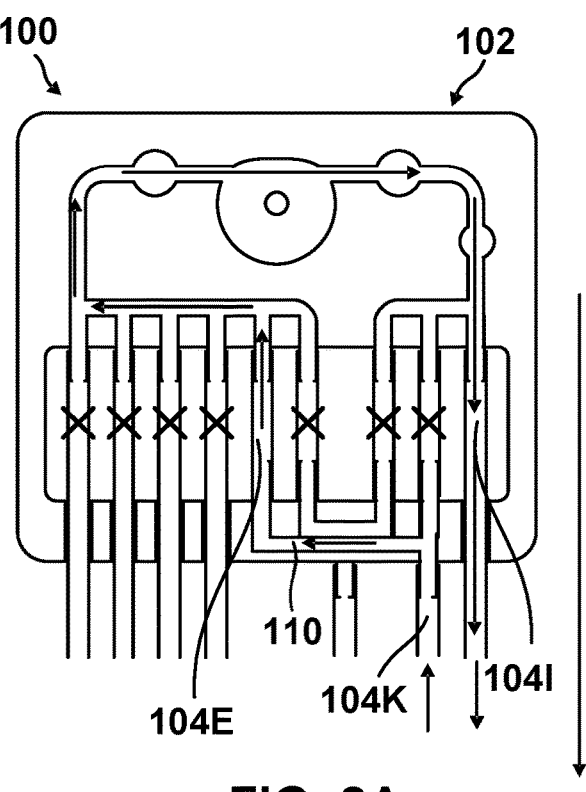
FIG. 8A
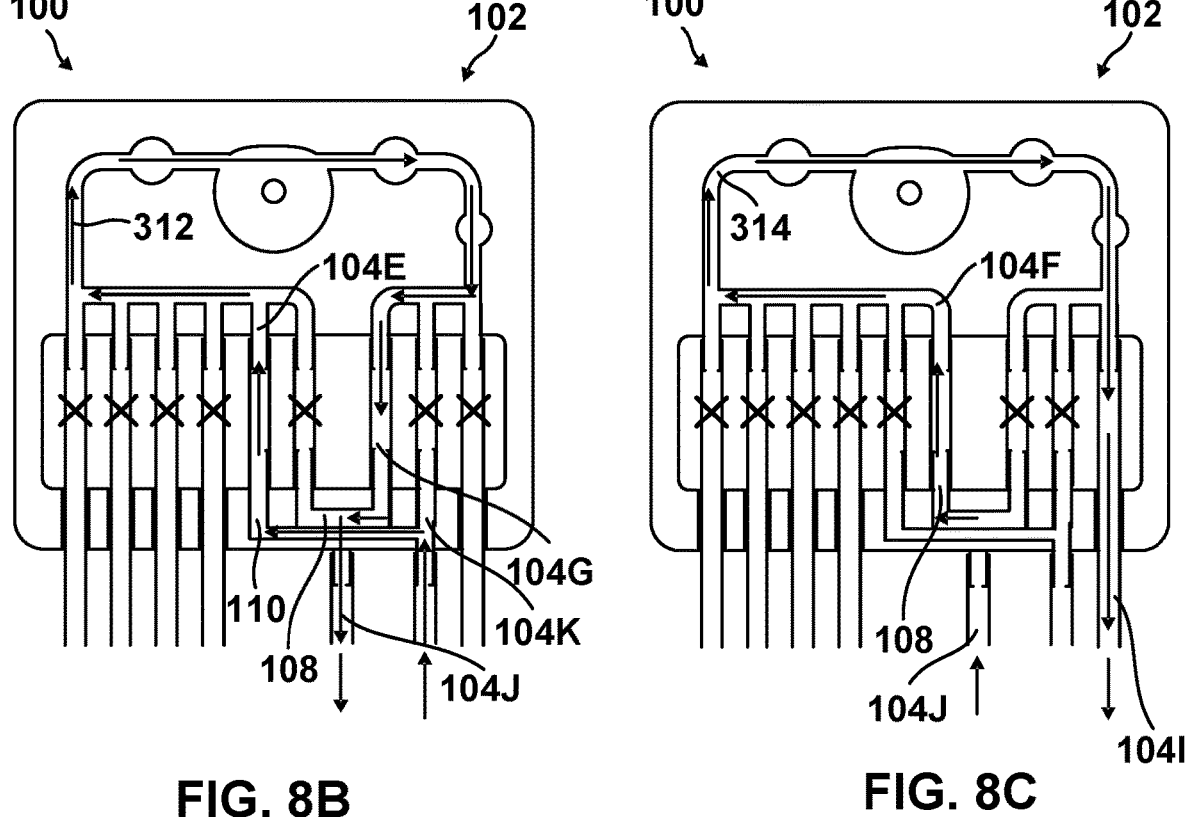
FIG. 8B           FIG. 8C

FORM A FIRST FLUID FLOW PATH THROUGH A PD CASSETTE — 1002

SELECT A SECOND FLUID FLOW PATH DEFINED BY THE PD CASSETTE — 1004

OCCLUDE AN UNOCCLUDED FLEXIBLE TUBE OF THE FIRST FLUID FLOW PATH VIA AN ACTUATOR TO FORM THE SECOND SELECTED FLOW PATH — 1006

UNOCCLUDE A DIFFERENT FLEXIBLE TUBE TO FORM THE SELECTED FLOW PATH — 1008

PERITONEAL DIALYSIS CASSETTE

TECHNICAL FIELD

The present disclosure relates to peritoneal dialysis (PD) systems.

BACKGROUND

Peritoneal dialysis (PD) may be used to remove waste products from blood of a patient when the kidneys of the patient are no longer able to adequately do so. During PD, a PD cycler delivers a dialysate through a catheter into a peritoneal cavity of a patient. The peritoneum of the patient acts as a membrane through which waste products are removed from the blood of the patient via osmosis and diffusion. Waste products and fluid pass from the blood of the patient, through the peritoneum, and into the dialysate. After a dwell period, the PD cycler removes an effluent fluid from the peritoneal cavity, which includes the dialysate and filtered waste products, from the patient's peritoneal cavity through the catheter.

SUMMARY

This disclosure describes example devices, systems, and techniques for routing fluids during PD, e.g., via PD cassettes configured to engage with a PD cycler. A PD cassette may be used as a disposable component of a PD system that defines a plurality of fluid flow paths between inputs and outputs of a fluid circuit including the peritoneal cavity of the patient. Physical/mechanical components of a PD device (also referred to herein as a PD cycler) may interact with the PD cassette to affect the fluid flow through the fluid circuit without physically contacting the fluid, thereby maintaining the sterility of the fluid and the fluid circuit. The cassette and connecting lines may be disposable and used once or a few times over a relatively short period of time, and replaced with a new, sterile cassette and connecting lines for subsequent therapy. The PD device may use the PD cassette as a fluid switch and/or direction control valve to select between the multiple inputs and outputs of the fluid circuit including the patient and the cassette, e.g., inputs/outputs such as PD bags including dialysate, dialysate conditioners such as heater bags, waste lines, and fluid lines connected to a catheter disposed within the peritoneal cavity of the patient.

In examples described herein, a PD cassette or cassette assembly includes a rigid member defining a plurality of fluid flow paths and a plurality of flexible tubes each defining a respective lumen and configured to be occluded via an externally applied pressure and unoccluded in the absence of the applied pressure. Each flexible tube is configured to be fluidically connected to a flow path of the rigid member, and together the rigid member and flexible tubes define a plurality of fluid flow paths through which fluid may be routed, e.g., during PD. Different fluid flow paths of the plurality of fluid flow paths are defined by occluding different flexible tubes of the plurality of flexible tubes, e.g., via one or more actuators under the control of control circuitry of a PD system.

In one example, this disclosure describes an article including a rigid member defining a plurality of fluid flow paths; and a plurality of flexible tubes each defining a lumen and configured to be occluded via a pressure applied externally to the respective lumen and unoccluded in the absence of the externally applied pressure, wherein each flexible tube is configured to be fluidically connected to a flow path of the plurality of flow paths, wherein different fluid flow paths of the plurality of fluid flow paths are defined by occluding different flexible tubes of the plurality of flexible tubes.

In another example, this disclosure describes a system including a cassette including a rigid member defining a plurality of fluid flow paths, each of the fluid flow paths including at least one fluidic connection to a fluid input or fluid output of the rigid member; and a plurality of flexible tubes each defining a lumen and configured to be occluded via a pressure applied externally to the lumen and unoccluded in the absence of the externally applied pressure, wherein each flexible tube is configured to be fluidically connected to a flow path of the plurality of fluid flow paths, wherein different fluid flow paths of the plurality of fluid flow paths are defined by occluding different flexible tubes of the plurality of flexible tubes; a peritoneal dialysis device comprising a plurality of actuators configured to apply the pressure externally to the plurality of flexible tubes; and control circuitry configured to selectively cause one or more actuators of the plurality of actuators to apply the pressure to or release the pressure from one or more flexible tubes of the plurality of flexible tubes.

In another example, this disclosure describes a method including selecting, via control circuitry, a fluid flow path of a plurality of fluid flow paths defined by a peritoneal dialysis cassette, the peritoneal dialysis cassette includes a rigid member defining a plurality of fluid flow paths, each of the fluid flow paths including at least one fluidic connection to a fluid input or fluid output of the rigid member; and a plurality of flexible tubes each defining a lumen and configured to be occluded via a pressure applied externally to the respective tube and unoccluded in the absence of the externally applied pressure, wherein each flexible tube of the plurality of flexible tubes is configured to be fluidically connected to a flow path of the rigid member, wherein different fluid flow paths of the plurality of fluid flow paths are defined by occluding different flexible tubes of the plurality of flexible tubes; and causing, via the control circuitry, one or more actuators to occlude at least one flexible tube of the plurality of flexible tubes to define the fluid flow path.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIG. 8A is a view of a first side of an example cassette illustrating another example flow path through the cassette.

FIG. 8B is a view of a first side of an example cassette illustrating another example flow path through the cassette.

FIG. 8C is a view of a first side of an example cassette illustrating another example flow path through the cassette.

DETAILED DESCRIPTION

Figure 1:
FIG. 1 is a diagram illustrating an example PD system configured to provide a patient with PD treatment.
Figure 1:
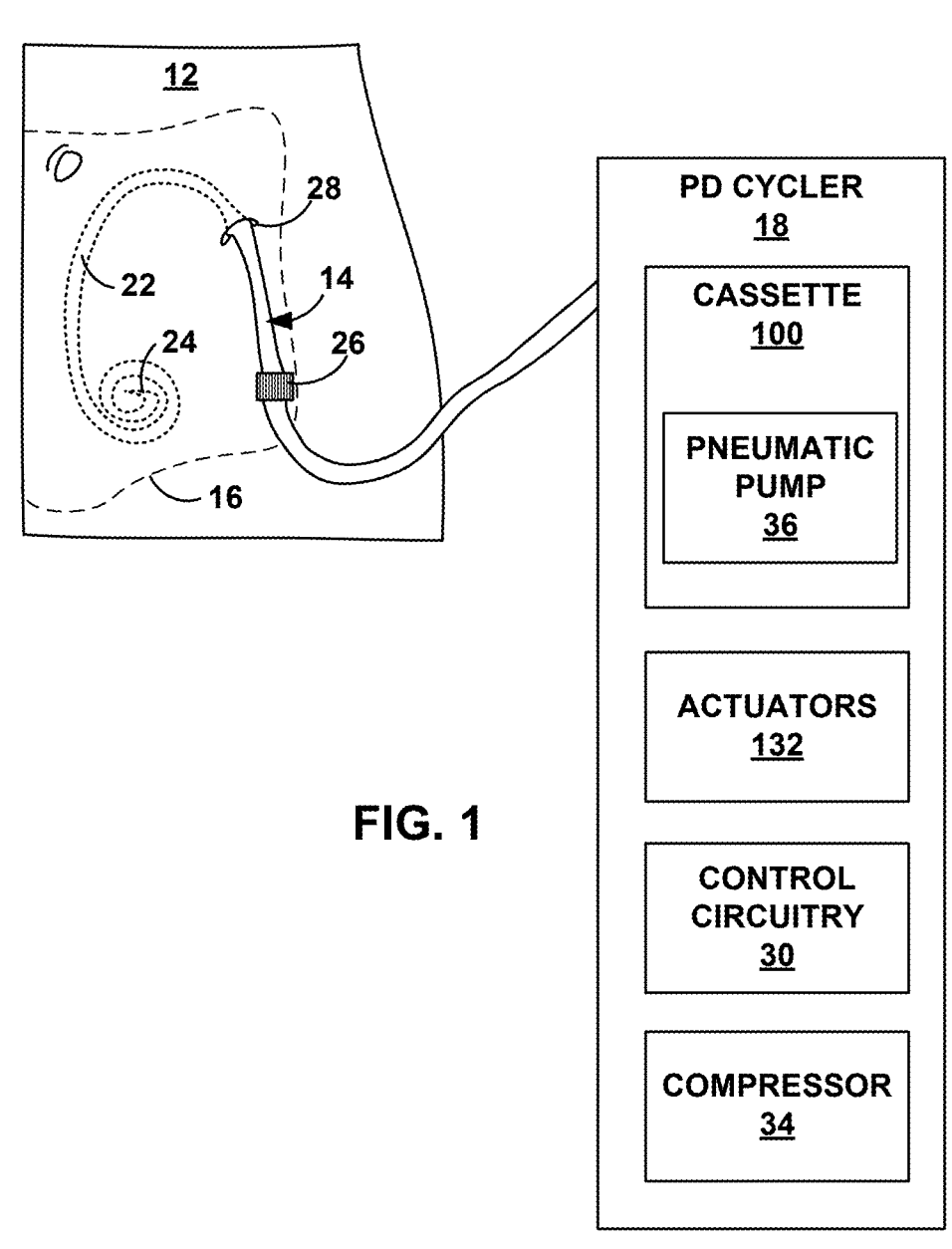

This disclosure describes example devices, systems, and techniques for routing fluids during PD, e.g., via PD cassettes for use with PD cyclers. In examples described herein, a PD cassette includes a rigid member defining a plurality of fluid flow paths and a plurality of flexible tubes each defining a respective lumen and configured to be occluded via a pressure applied externally to the respective tube and unoccluded in the absence of the externally applied pressure. Each flexible tube is configured to be fluidically connected to a flow path of the rigid member, and together the rigid member and flexible tubes define a plurality of fluid flow paths through which fluid may be routed, e.g., during different stages of PD therapy. Different fluid flow paths of the plurality of fluid flow paths are defined by occluding different flexible tubes of the plurality of flexible tubes. In some examples, control circuitry of a PD system controls a plurality of actuators to selectively apply external pressure to different tubes of the plurality of tubes to define different fluid flow paths through the cassette (and PD system). By controlling the plurality of actuators to apply the external pressure to different tubes over time, the control circuitry can cause fluid to flow through different flow paths of the PD cassette to facilitate delivery of PD therapy to a patient.

Automated peritoneal dialysis (APD) uses a machine, called a cycler or a PD cycler, to automatically infuse, dwell, and drain peritoneal dialysis solution to and from a patient's peritoneal cavity. APD may be performed at night while the patient is asleep. Some APD sequences can last for several hours and often begins with an initial drain cycle to empty the peritoneal cavity of spent dialysate. The APD sequence then proceeds through a succession of fill, dwell, and drain phases occurring in sequential order. Each fill/dwell/drain sequence may be referred to as a PD cycle. During the fill phase, the PD cycler transfers a predetermined volume of fresh, warmed dialysate into the peritoneal cavity of the patient. The dialysate remains (or "dwells") within the peritoneal cavity for a time during the dwell phase. During the drain phase, the PD cycler removes effluent fluid, including the dialysate and waste, from the peritoneal cavity of the cavity. The number of fill/dwell/drain cycles that are required during a given APD session depends upon the total volume of dialysate prescribed for the patient.

The PD cycler transfers fluids between the peritoneal cavity of the patient and a plurality of inputs and outputs, such as by selectively fluidically connecting one or more inputs with one or more specific outputs to create a desired fluid flow path through the PD system. For example, the inputs may be one or more fresh bags of PD dialysate, a heater bag and/or fluid heating apparatus, the peritoneal cavity of the patient, and waste bags and/or a waste drain line. The PD cycler may be configured to cause fluid to move, e.g., via a pumping mechanism, through tubing fluidically connected to the cassette. The cassette defines a plurality of fluid pathways (also referred to herein as fluid flow paths or flow paths) configured to fluidically interconnect the various inputs and outputs. In some examples, the cassette may include the pumping mechanism, e.g., one or more pneumatic pumps, such as one or more diaphragms, configured to cause fluid to move through a fluid circuit defined at least in part by the cassette.

In some examples, the inputs, outputs, tubing, and cassette connecting the inputs and outputs are fluidically separated from the PD cycler. For example, the tubing and the cassette may be disposable, and the PD cycler, e.g., compressor, actuators, control circuitry and the like, may be isolated from any fluids to maintain sterility of the fluids. In some examples, the PD cycler includes an air compressor configured to cause a pumping mechanism, e.g., a diaphragm pump or any other suitable pumping mechanism, to operate to move fluid and one or more actuators configured to engage with the cassette and select between one or more fluid pathways defined at least in part by the cassette. For example, the actuators can physically engage with certain parts of the cassette to selectively cause fluid to flow through one or more specific fluid pathways defined at least in part by the cassette and not flow through other one or more fluid pathways. The use of such a cassette may eliminate the need for directional control valves, which may simplify the PD cycler.

For example, some cassettes currently being used include a flexible membrane disposed over a plurality of fluid channels defined by a body of the cassette. The one or more actuators of the PD cycler may be configured to depress the flexible membrane at one or more positions in the fluid channels of the cassette thereby blocking the fluid channel. Other fluid channels may be left open, and the PD cycler may select between a plurality of pathways between the various inputs and outputs by closing/opening certain channels in the cassette. In this way, no portion of the PD cycler may come into contact with the fluid, thereby maintaining the sterility of the fluids between the inputs, outputs, and peritoneum of the patient.

A pressure is applied to the membrane of the cassette in order for the cassette to define the one or more flow paths, e.g., to seal the membrane to structures of the cassette in order to define the fluid flow paths. For example, a single rigid body of the cassette may include a plurality of recessed channels, and a flow path may be defined by pressing a membrane to one or more surfaces of the rigid body such that the recessed channels are sealed by the membrane forming the one or more fluid pathways.

A PD cycler may include a cassette or cassette assembly in which the cassette is placed in the PD device with one or more channels aligned with one or more actuators configured to depress at least a portion of the membrane into one or more channels (or otherwise against a rigid surface) to block one or more fluid pathways, and the PD device may be configured to simultaneously apply a pressure to the membrane (e.g., via a support plate and a face plate) to seal the channels. If the pressure on the membrane is released during filling/draining, then fluid may leak from one fluid pathway to another within the cassette, the cassette diaphragm pump may not be able to provide a pressure differential to move fluid, or both. For example, if the cassette mounting assembly is opened during a fill/drain phase of a cycle, then PD dialysate may leak into a fluid pathway bypassing the patient and directly into a waste bag, or fluid from the patient including waste may leak into fresh PD dialysate bags or back into the peritoneum of the patient. Additionally, a relatively large air compressor may be required to maintain the pressure on the membrane. Further, the membrane may need to be relatively thin and may be susceptible to splitting, breaking, or otherwise failing after a number of PD cycles, e.g., a number of depressions by an actuator.

The PD cassettes described herein may address one or more these issues with PD cassettes that include depressible membranes for fluid pathway definition through the cassette. According to examples disclosed herein, a PD cassette (also referred to herein as a or cassette assembly in some examples) includes a rigid member defining a plurality of fluid flow paths and a plurality of flexible tubes each defining a lumen and configured to be occluded via an applied pressure and unoccluded in the absence of the applied pressure. When occluded via the externally applied pressure, fluid flow through the respective flexible tube is substantially blocked (e.g., fully blocked or nearly fully blocked to effectively block meaningful fluid flow through the tube). Each flexible tube defines at least a portion of a fluid flow path of the plurality of flow paths defined by the rigid member, and each of the tubes may function as a valve for fluid flow along the respective fluid flow path including that particular tube. In other words, the PD cassette may use the flexible tubes rather than a flexible membrane and rigid cassette body, and, in some examples, the PD cassette does not include a flexible membrane. In some examples, the rigid member is sufficiently stiff such that it cannot be depressed to occlude the plurality of fluid flow paths defined by the rigid membrane without adversely impacting the structural integrity of the rigid member (e.g., without breaking the rigid member).

In some examples, a PD cassette including flexible tubes as valves rather than a flexible membrane may reduce leaking and/or risk of leaks between fluid flow paths because the flexible tubes may be relatively thicker than a flexible membrane. As such, the flexible tubes may be able to withstand a larger pressure to occlude the lumen of the tubes than a comparative membrane and for a given number of occlusions/depressions, e.g., the tubes may last longer than a comparative membrane. Further, the comparatively larger pressure that many be used with flexible tubes as opposed to a PD cassette utilizing a membrane may reduce leaking.

While cassettes with membranes are useful, the cassettes described herein can provide one or more technical advantages. For example, the cassettes described herein are not used as a rigid backing for application of pressure to occlude a pathway and may have an improved lifetime and/or improve the number of occlusions/depressions and or time that a particular channel/pathways may be occluded. An actuator depressing a membrane depresses the membrane to contact a rigid cassette body of the cassette in order to occlude the pathway. By contrast, according to the systems, device, and methods disclosed herein, an actuator may depress a flexible tube against a rigid material (e.g., a rigid plate) that is separate from the cassette, e.g., essentially squeezing or pinching the flexible tube shut to occlude the tube and modify a fluid flow path through the available fluid flow paths of the cassette.

The example devices, systems, and techniques may provide further technical advantages. For example, the occlusion of a flexible tube may be easier to implement and more accurate, e.g., more accurate for both positioning of an actuator to occlude a tube, and more accurate for occluding the tube without leaks. In some examples, example devices, systems, and techniques disclosed herein may provide for a PD cycler with reduced and/or fewer components. For example, the number of flow paths may be reduced, further reducing opportunity for leaks to occur and reducing the number of actuators needed and reducing the air pressure demand of the system. Further, example devices, systems, and techniques may provide for a PD cycler with improved reliability because of the elimination of the need to seal a membrane to the cassette body to define the flow paths, reducing opportunity of leaks and further reducing the air pressure demand of the system, allowing for the use of a smaller compressor.

In some examples disclosed herein, a cassette may have a flexible tube associated with each input and output of the PD cycler. Control circuitry of a PD system is configured to control one or more actuators to selectively occlude each flexible tube to stop a flow of fluid to or from its associated input/output. All of the fluid inputs and outputs may be fluidically interconnected within the cassette via a plurality of fluid pathways, and the cassette may include a pneumatic pump (e.g., a diaphragm pump or the like) to provide motive force to a fluid of the inputs/outputs to move fluid through the plurality of pathways. Each flexible tube may function as a type of fluid switch and/or direction control valve, and the control circuitry can select a pathway of the plurality of pathways by selectively turning "on" (e.g., unoccluding, such as by controlling one or more actuators to release an externally applied pressure) and turning "off" (occluding, such as by controlling one or more actuators to apply the external pressure) one or more flexible tubes, e.g., switches/valves.

As an example, a cassette may include a plurality of inputs from a plurality of PD dialysate bags, an input/output (I/O) to/from a patient, e.g., a patient I/O line via a fluidic connection to a catheter placed within the peritoneal cavity of the patient), and a waste line output. Control circuitry can cause fluid to be transferred to the patient through the cassette by controlling one or more actuators of a plurality of actuators to unocclude at least one of the flexible tubes associated with an input line and the patient I/O line, and controlling one or more actuators of the plurality of actuators to occlude all other inputs/outputs via occluding their associated flexible tube, thereby selecting a fluid pathway within the cassette from a PD dialysate bag to the patient. After a dwell time, the control circuitry can cause effluent to be removed from the patient by at least causing one or more actuators of the plurality to occlude the flexible tube of each input dialysate line, and cause one or more actuators of the plurality of actuators to unocclude the flexible tube of the waste line output and the patient I/O line, thereby selecting a fluid pathway within the cassette from the patient to the waste line.

FIG. 1 is a diagram illustrating an example PD system 10 configured to provide patient 12 with PD treatment. PD system 10 includes a catheter 14, which is illustrated as extending into a peritoneal cavity 16 of patient 12, and a PD cycler 18, which includes a cassette 100, one or more actuators 132, and control circuitry 30. In other examples, control circuitry 30 can be separate from PD cycler 18, but still configured to control operation of one or more aspects of PD cycler 18, such as the operation of actuators 132 of PD cycler 18, described in further detail below.

PD cycler 18 is configured to deliver a dialysate into peritoneal cavity 16 via catheter 14. The dialysate remains in peritoneal cavity 16 for a dwell period, which has a duration that is intended to, but may not always be, sufficient for the exchange of waste products across a peritoneum of patient 12 to take place. In some such examples, PD cycler 18 may be disconnected from catheter 14 during the dwell period. In other examples, however, PD cycler 18 remains connected to catheter 14 during the dwell period. After the dwell period, PD cycler 18 removes fluid from peritoneal cavity 16. The fluid drained from peritoneal cavity 16 can be referred to as an effluent fluid, which contains the dialysate and the waste products removed from the blood of patient 12. In some examples, PD cycler 18 may be active cycler configured to move fluid via a pump. In other examples, PD cycler may be a passive cycler configured to move fluid via gravity.

Waste products may be removed from the bloodstream of patient 12 by the dialysate via an osmosis, e.g., a concentration gradient of an osmotic agent across the peritoneum of patient 12. A higher concentration of the osmotic agent created in peritoneal cavity 16 by filling peritoneal cavity 16 with dialysate including a concentration of the osmotic agent drives ultrafiltration and convective solute removal. The dialysate may include water, and dextrose or other sugars, salt, electrolytes, ions, amino acids, glucose polymers, and/or minerals as the osmotic agent. In some examples, the dialysate is dextrose-based, e.g., includes dextrose as the osmotic agent. Examples of dextrose-based dialysates include, but are not limited to, Dianeal available from Baxter Healthcare Corporation of Deerfield, IL and Delflex® available from Fresenius Medical Care of Waltham, MA. In other examples, the dialysate may be characterized in having relatively low amounts of glucose degradation products (GDPs) and/or having a neutral pH (e.g., a pH of or close to 7). Examples of such dialysates include, but are not limited to, Physioneal available from Baxter Healthcare Corporation of Deer Field, IL, balance available from Fresenius Medical Care of Waltham, MA, and bicaVera® available from Fresenius Medical Care of Waltham, MA. In yet other examples, dialysates may be icodextrin-based, such as Extraneal available from Baxter Healthcare Corporation of Deer Field, IL, or amino acid-based, such as Nutrineal™ available from Baxter Healthcare Corporation of Deer Field, IL.

In order to deliver the dialysate into peritoneal cavity 16 and remove the effluent fluid from peritoneal cavity 16, PD cycler 18 is connected to catheter 14, such as via an adapter 26, which provides the necessary mechanical connection between catheter 14 and PD cycler 18 to establish fluid communication therebetween. Catheter 14 may be any fluid delivery conduit capable of being inserted into peritoneal cavity 16 and connected to PD cycler 18 to facilitate PD treatment of patient 12. Catheter 14 defines an inner lumen 22 through which fluid may flow from PD cycler 18 to peritoneal cavity 16 and from peritoneal cavity 16 to PD cycler 18. Inner lumen 22 terminates at a distal opening, which can be at a distal-most end 24 of catheter 14, as shown in FIG. 1, and/or along a sidewall proximal to the distal-most end of catheter 14. Catheter 14 may be inserted into patient 12 via an exit site 28, and be configured to remain in patient 12 on a long-term basis.

Catheter 14 can have any suitable configuration. For example, the portion of catheter 14 that remains within peritoneal cavity 16 may be straight or curvilinear, such as coiled (e.g., pig-tailed) as shown in FIG. 1. In some examples, a distal portion of catheter 14 has a swan neck (e.g., a curved portion 40, shown in FIGS. 2 and 3, curved up to about 180 degrees), which may help position catheter 14 at exit site 28 as intended. Catheter 14 has any suitable length for accommodating PD treatment. For example, catheter 14 may be between about 57 cm and about 62 cm in length (e.g., from adapter 26 to a distal-most end of catheter 14 within peritoneal cavity 16), and may be between about 2.5 mm and about 3.5 mm in diameter. In other examples, other shapes, sizes (e.g., length or diameter), and/or configurations may be used. An example of catheter 14 includes, but is not limited to, the Argyle™ Peritoneal Dialysis Catheter available from Medtronic, Inc. of Minneapolis, MN.

In order to deliver the dialysate into peritoneal cavity 16 and remove the effluent fluid from peritoneal cavity 16, PD cycler 18 is configured to house and interact with PD cassette 100. PD cycler 18 includes assemblies configured to hold the cassette, assemblies configured to hold actuators 132 configured to occluded one or more respective flexible tubes of cassette 100, e.g., to select and deselect flow paths within cassette 100, and assemblies to operate a pump that causes fluid to flow through fluid pathways of cassette 100. In some examples, cassette 100 further includes one or more sensors configured to sense a fluid parameter, e.g., a pressure sensor configured to sense a fluid pressure within the cassette and/or a fluid pathway, a temperature sensor configured to sense a temperature of a fluid within the cassette and/or a fluid pathway, and the like.

In examples described herein, cassette 100 includes a rigid member defining a plurality of flow paths. Cassette 100 also includes a plurality of flexible tubes each defining a lumen that is configured to be occluded via a pressure applied externally to the respective flexible tube and unoccluded in the absence of the externally applied pressure. Each flexible tube is configured to be fluidically connected to a flow path of the rigid member, and control circuitry 30 is configured to define different fluid flow paths through cassette 100 by causing different flexible tubes to be occluded or unoccluded. Fluid flows through different fluid flow paths of cassette depending on which flexible tubes are occluded or unoccluded.

In some examples, PD cycler 18, under the control of control circuitry 30, is configured to occlude each flexible tube via an actuator 132, e.g., a pneumatic actuator, a mechanical actuator, a solenoid, and the like. Each flexible tube may be configured to be occluded via an actuator 132, e.g., the flexible tube is configured to collapse and close the lumen of the flexible tube upon application of the externally applied pressure to the tube via an actuator 132. In some examples, the externally applied pressure configured to close the lumen of the flexible tube is proportional to the hardness of the flexible tube. In some examples, the flexible tube may have a durometer corresponding to a Shore 00 or a Shore A hardness. For example, the flexible tube may have a Shore hardness between Shore A 40 and Shore A 80, or between Shore A 20 and Shore A 90, or between Shore A 0 and Shore A 100. In some examples, the externally applied pressure configured to close the lumen of the flexible tube is greater than or equal to 10 newtons (N) and less than or equal to 15N. In some examples, the externally applied pressure may be greater than 15N or less than 10N, and in general corresponds to the hardness of the flexible tube and is configured to be at least the minimum pressure sufficient to close the lumen of the flexible tube.

In some examples, cassette 100 further includes a pump and at least one sensor configured to sense one or more fluid parameters of a fluid in a fluid flow path of cassette 100. For example, cassette 100 may include a diaphragm pump (e.g., pneumatic pump 36) configured to provide motive force to a fluid within a flow path of cassette 100. Cassette 100 may include any other type of pump, e.g., a dynamic pump, a centrifugal pump, a kinetic pump, a positive displacement pump, a reciprocating pump, a rotary pump, a piston or plunger pump, and the like. In some examples, cassette 100 may include more than one pump of the same type of different types. In some examples, cassette 100 may include a temperature sensor configured to sense a temperature of a fluid within a flow path of cassette 100 and/or a pressure sensor configured to sense a pressure of a fluid within a flow path of cassette 100. In addition to or instead of the temperature and/or pressure sensors, cassette 100 may include any other suitable sensor configured to sense a fluid parameter of a fluid within a flow path of cassette 100.

In some examples, the rigid member of cassette 100 includes a first rigid member and a second rigid member connected together. For example, the first rigid member may be a front half of the rigid member and the second rigid member may be a back half. In some examples, the first and second rigid members, when connected together, define a plurality of channels that form the plurality of fluid flow paths when the first and second rigid members are connected together. In some examples, the first rigid member and the second rigid member are connected together via laser welding, ultrasonic welding, hot plate welding, a mechanical fastener, an adhesive, a compression fitting, a friction fit, or any suitable connection method, component, or apparatus, or combinations thereof.

The rigid member of cassette 100 defines or otherwise includes one or more fluidic connectors defining entry points into or exit points from one or more of the plurality of fluid pathways defined by the rigid member. For example, the rigid member may define a fluidic connector to each flow path of the plurality of fluid flow paths, e.g., defined by the channels. Each flexible tube of the plurality of flexible tubes may be configured to mechanically connect to a respective fluidic connector using any suitable technique, such as by at least one of a friction fit or a heat seal. When so mechanically connected, the flexible tube is in fluid communication with the fluid connector and respective fluid flow path. In some examples, a flow path may have both a first and second fluidic connector configured to be connected each to an end of a flexible tube. In other words, one or more flow paths defined by cassette 100 may have a portion of the flow path comprised of the flexible tube, e.g., a channel defining a flow path may have a gap that is "bridged" by a flexible tube fluidically connected to the first and second fluidic connectors.

In some examples, cassette 100 is configured to reduce the number of flow paths interconnected within cassette 100, thereby allowing PD cycler 18 to be configured to reduce the number of actuators 132 to occlude a flow path, e.g., via occluding a flexible tube. In some examples, cassette 100 includes ten or fewer fluid flow paths configured to selectively interconnect a plurality of external fluid connections (e.g., inputs and/or outputs to cassette 100). The plurality of external fluid connections may include at least one patient fluid connection, e.g., a patient I/O line, at least one dialysate fluid connection, e.g., a PD dialysate input, at least one drain fluid connection, e.g., an effluent waste line, and at least one fluid heating fluid connection, e.g., a PD heater bag I/O line.

In the example shown, PD cycler 18 includes control circuitry 30. Control circuitry 30 is configured to control PD cycler 18 to deliver PD therapy to patient 12 during a PD cycle. For example, control circuitry 30 may cause PD cycler 18 to deliver a dialysate into peritoneal cavity 16 via catheter 14 and may cause PD cycler 18 to remove fluid from peritoneal cavity 16 via catheter 14, e.g., after a dwell time.

Control circuitry 30 may be configured to select a fluid flow path defined by cassette 100, such as by controlling actuators 132 to selectively occlude or unocclude different flexible tubes of cassette 100 to achieve a desired flow path through cassette 100. For example, upon initiation of PD therapy, control circuitry 30 may be configured select a first fluid flow path to deliver PD dialysate from a PD dialysate input such as a PD dialysate bag to a heater bag in preparation for delivery of the PD dialysate to patient 12. Control circuitry 30 can control one or more actuators 132 (a "first set" of actuators 132) to selectively occlude one or more flexible tubes (a "first set" of flexible tubes) to achieve the selected first fluid flow path through cassette 100. After a heating time, control circuitry 30 may select a second and different fluid flow path to deliver the heated PD dialysate form the heater bag to patient 12. Control circuitry 30 can control one or more actuators 132 (a "second set" of actuators 132) to occlude one or more flexible tubes (a "second set" of flexible tubes) to achieve the selected second fluid flow path through cassette 100. After a dwell time, control circuitry 30 may be configured to select a third fluid flow path different from the first and second fluid flow paths to deliver effluent from patient 12 to a waste line. Control circuitry 30 can control one or more actuators 132 (a "third set" of actuators 132) to occlude one or more flexible tubes (a "third set" of flexible tubes) to achieve the selected third fluid flow path through cassette 100. In some examples, control circuitry 30 can control one or more subsets of actuators 132 (e.g., one or more actuators), or one or more subsets of first, second, or third sets of actuators 132, to activate and occlude or deactivate and unocclude one or more subsets of flexible tubes.

The first, second, and third sets of actuators 132 can differ from each other by at least one actuator and, in some examples, do not have any common actuators. Similarly, first, second, and third sets of flexible tubes can differ from each other by at least one flexible tube and, in some examples, do not have any common flexible tubes. Thus, to define a particular fluid flow path through cassette 100, in some cases, control circuitry 30 not only causes a set of flexible tubes to be occluded, but may also cause one or more actuators 132 to release the pressure applied to one or more other flexible tubes, e.g., to cause a set of flexible tubes to be unoccluded.

Control circuitry 30 may be configured to cause an actuator 132 to occlude a flexible tube to form the selected flow path using any suitable technique. For example, control circuitry 30 may send a signal to a compressor 34 to provide air or air pressure to one or more pneumatic actuators 132, and control circuitry 30 may send a signal to one or more actuator 132, e.g., a command signal, to activate those one or more of the actuators 132 to occlude a flexible tube. Control circuitry 30 may additionally send a command signal to one or more actuators 132 to deactivate those one or more actuators 132. By causing actuators 132 to occlude and unocclude different flexible tubes, control circuitry 30 may form the differing fluid flow paths through cassette 100.

In some examples, control circuitry 30 is configured to receive one or more signals generated by PD cycler 18 and/or a sensor, e.g., a sensor of cassette 100, and determine information about PD system 10 and/or patient 12 based on the received signals. The information about PD system 10 can include, for example, one or more PD parameters of PD cycler 18. The determination of such information about PD system 10 or patient 12 may be used to deliver and/or adjust the PD treatment delivered by PD cycler 18 via cassette 100.

Control circuitry 30, as well as other processors, processing circuitry, controllers, control circuitry, and the like, described herein, may include any combination of integrated circuitry, discrete logic circuity, analog circuitry, such as one or more microprocessors, digital signal processors (DSPs), application specific integrated circuits (ASICs), or field-programmable gate arrays (FPGAs). In some examples, control circuitry 30 may include multiple components, such as any combination of one or more microprocessors, one or more DSPs, one or more ASICs, or one or more FPGAs, as well as other discrete or integrated logic circuitry, and/or analog circuitry.

In some examples, control circuitry 30 can be part of PD cycler 18, while in other examples, control circuitry 30 can be part of a different device, such as a clinician computer that is located near PD cycler 18 or remotely located (e.g., more than 50 feet away) from PD cycler 18. Although not shown in FIG. 1, control circuitry 30 may be part of a device that includes additional components, such as, but not limited to, a memory, a telemetry module that includes circuitry to facilitate communication between control circuitry 30 and another component, such as a power source.

PD cycler 18 may be configured to communicate with control circuitry 30 using any suitable communication technique and via any suitable wired or wireless communication channels. In examples in which control circuitry 30 is external to PD cycler 18 (e.g., as part of a separate device), PD cycler 18 communicates with control circuitry 30 via wireless signals. Control circuitry 30 and PD cycler 18 may communicate using any of a variety of local wireless communication techniques, such as radio frequency (RF) communication according to the 802.11 or Bluetooth® specification sets, infrared (IR) communication according to the IRDA specification set, or other standard or proprietary telemetry protocols, or via remote telemetry such as, for example, via a local area network (LAN), wide area network (WAN), public switched telephone network (PSTN), or cellular telephone network.

Control circuitry 30 may also communicate with another computing device via a wired or wireless connection using any of any of the local or remote wireless communication techniques discussed with respect to communication between PD cycler 18 and control circuitry 30. Control circuitry 30 may also communicate with other computing devices via exchange of removable media, such as magnetic or optical disks, memory cards, or memory sticks.

Figure 2:
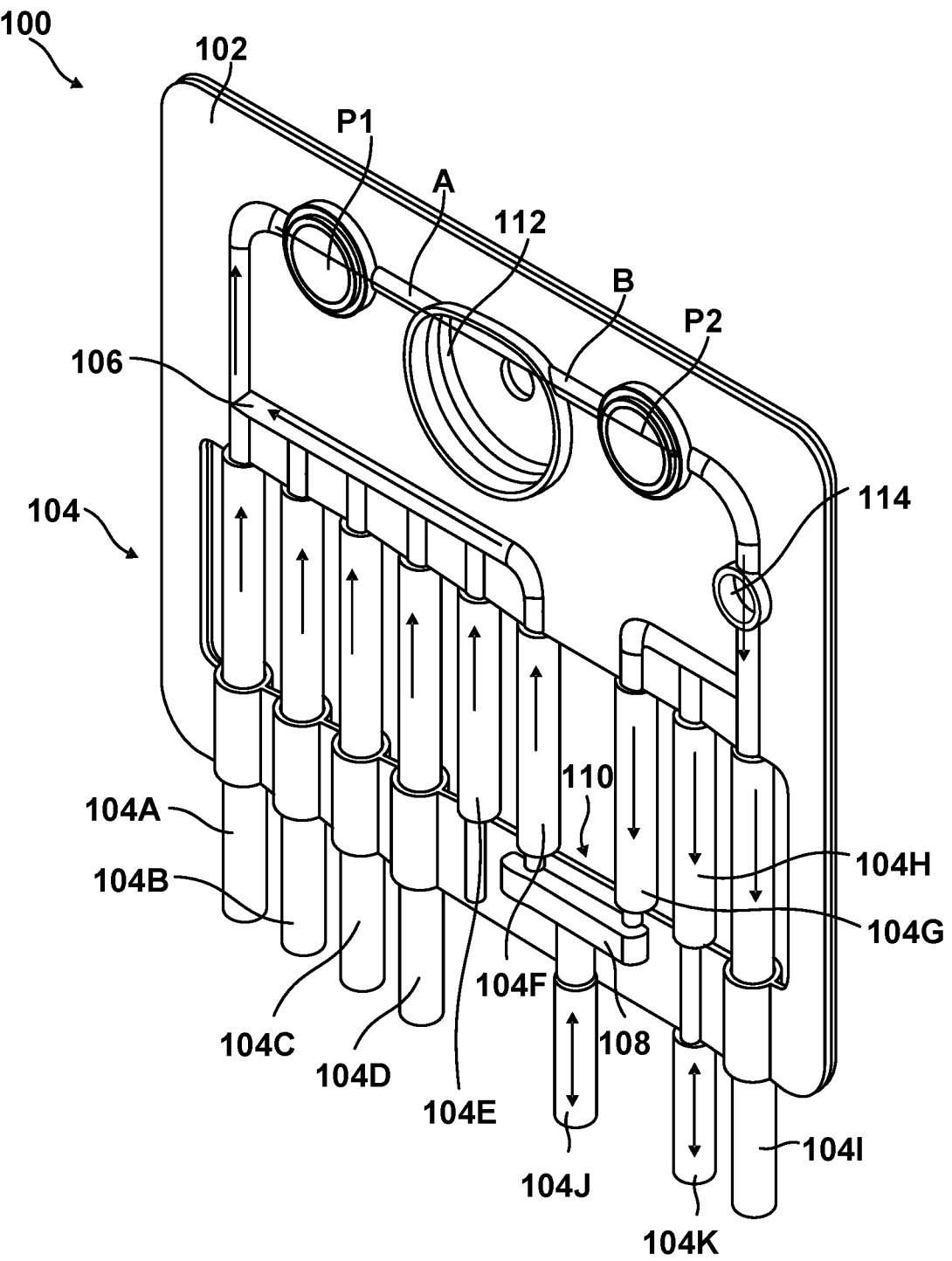
FIG. 2 is a perspective view of an example PD cassette.
Figure 3:
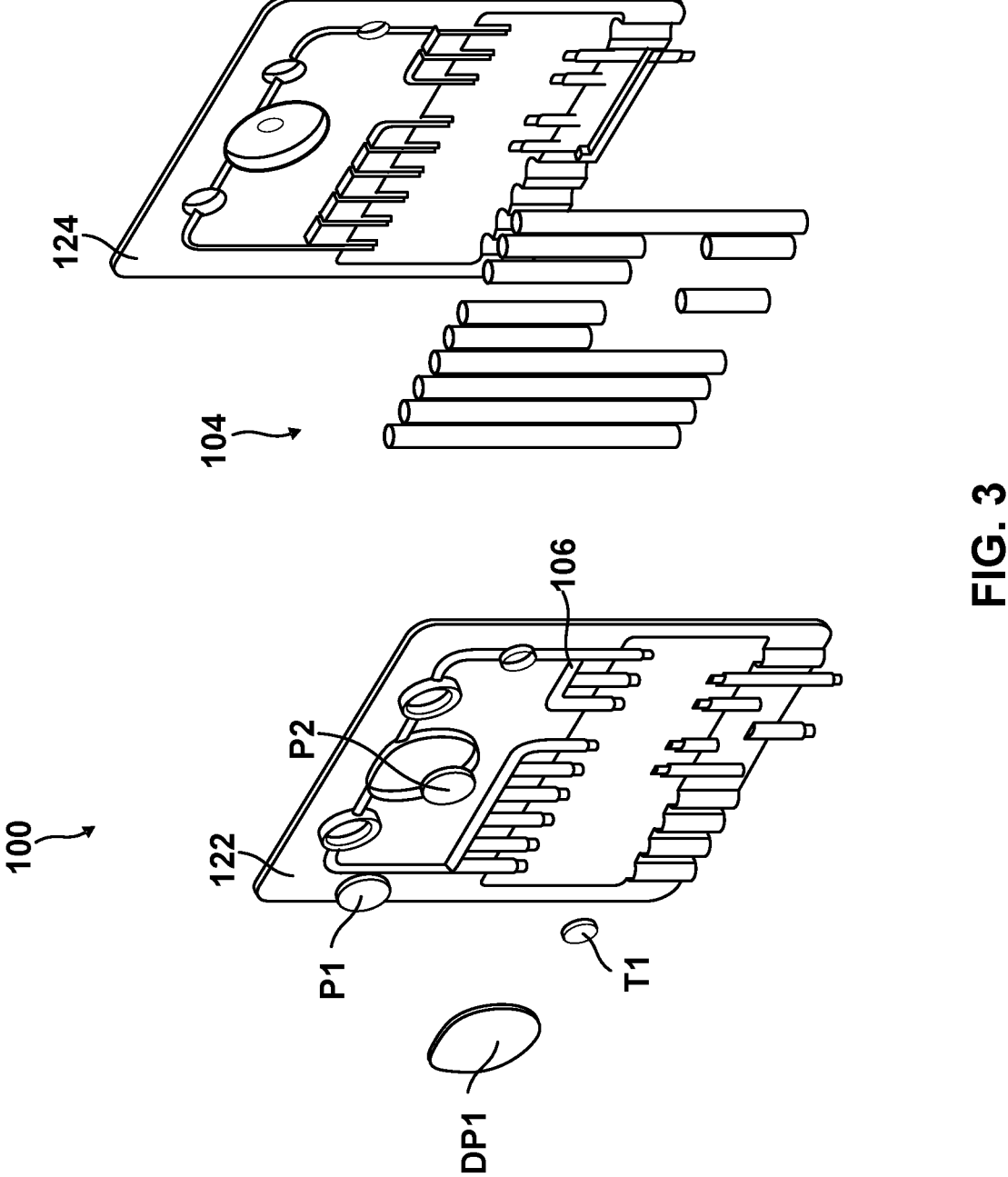
FIG. 3 is an exploded perspective view of the example PD cassette of FIG. 2.

FIG. 2 is a perspective view of an example PD cassette 100. FIG. 3 is an exploded perspective view of the example PD cassette 100 of FIG. 2. FIGS. 2 and 3 are described concurrently below.

PD cassette 100 includes rigid member 102, flexible tubes 104A-104K, collectively and/or generally referred to as flexible tubes 104, fluid flow channels 106-110, pressure sensors P1 and P2, diaphragm pump cavity 112, and temperature sensor cavity 114. In other examples, PD cassette 100 may include only pressure sensors P1, P2, or only a temperature sensor, or neither of the pressure or temperature sensors.

In the example shown, rigid member 102 includes channels 106-110, e.g., channels 106-110 are integral to rigid member 102 and defined by the structure of rigid member 102. Rigid member 102 may be made of any suitably rigid material, e.g., a solid such as a plastic, a metal, a rubber, and the like, and is configured to be self—supporting. In some examples, rigid member 102 may be formed of a first rigid member and a second rigid member connected together, e.g., first rigid member 122 and second rigid member 124, as illustrated in FIG. 3. In some examples, channels 106-110 may be embossed on or within rigid member 102. For example, each of first rigid member 122 and second rigid member 124 may have embossed opposing recesses such that channels 106-110 comprise one or more lumens, and/or a network of lumens, when first rigid member 122 and second rigid member 124 are connected. In the example shown, channels 106-110 define a plurality of fluid flow paths, e.g., from a plurality of fluid inputs and fluid outputs.

Flexible tubes 104 each define a respective lumen and are configured to be occluded via a pressure applied externally to the respective flexible tube (e.g., to an outer surface of the tube), and unoccluded in the absence of the externally applied pressure. The externally applied pressure causes the lumen of the tube 104 to collapse and prevent fluid flow through the lumen. In some examples, flexible tubes 104 are elastic, such that in response to removal of the externally applied pressure, the flexible tube assumes its open configuration such that fluid can flow through the lumen. Flexible tubes 104 may be made from any suitable material, such as, but not limited to, of a plastic, a polymer, a natural and/or synthetic rubber, an elastomer, nitrile rubber, silicone rubber, urethane rubber, a polyvinyl, polyvinyl chloride (PVC), thermoplastic polyurethane (TPU), or any suitably elastic material or combination thereof.

Flexible tubes 104 are configured to be fluidically connected to rigid member 102. In the example shown, cassette 100 includes four inputs corresponding to flexible tubes 104A-104D, one output corresponding to flexible tube 104I, and two input—outputs (I/Os) corresponding to flexible tubes 104J-104K. For example, flexible tubes 104A-104D may be configured to be fluidically connected between a respective PD dialysate bag and channel 106. That is, flexible tubes 104A-104D may define a fluid pathway from the PD dialysate bag to channel 106 in rigid member 102. In the example shown in FIG. 2, flexible tube 104I is configured to be fluidically connected between channel 106 and a waste/drain line, flexible tube 104J is configured to be configured to be fluidically connected between channel 108 and patient 12, and flexible tube 104K is configured to be fluidically connected between channel 110 (not visible in FIGS. 2 and 3 but illustrated in FIG. 5, e.g., visible on the opposite side of rigid member 102) and a heater bag. Flexible tubes 104E and 104H are configured to be fluidically connected between channel 106 and channel 108, and flexible tubes 104F-104G are configured to be fluidically connected between channel 106 and channel 110. In the examples shown, flexible tube 104E corresponds to an input fluid flow path from a heater bag via flexible tube 104K and flexible tube 104H corresponds to an output fluid flow path to the heater bag via flexible tube 104K. Similarly, flexible tubes 104F corresponds to an input fluid flow path from a patient (e.g., patient 12) via flexible tube 104J and flexible tube 104G corresponds to an output fluid flow path to the patient via flexible tube 104J.

The specific fluid flow paths defined by rigid member 102 and shown in FIG. 2 is one nonlimiting example, and rigid member 102 can define other fluid flow paths in other example. FIGS. 6, 7A-7D, and 8A-8C illustrate a plurality of differing fluid flow paths defined by rigid member 102 and flexible tubes 104.

Rigid member 102, or first rigid member 122 and second rigid member 124 when connected together, is configured to define a recess and/or cavity configured to be covered by pressure sensor membranes P1 and P2, e.g., to house and/or form pressure sensors configured to sense a pressure of a fluid flowing within channel 106. Rigid member 102, or first rigid member 122 and second rigid member 124 when connected together, is further configured to define a recess/cavity 112 configured to be covered by pump door DP1 and configured to define a recess/cavity 114 configured to be covered by a temperature sensor door T1, e.g., to house and/or form a diaphragm pump configured to provide a motive force to cause a fluid to flow through channel 106 and to house and/or form a temperature sensor configured to sense a temperature of a fluid flowing within channel 106. The direction of the motive force provided by the diaphragm pump is illustrated in FIGS. 2-8 as the directional arrows within channel 106. In the examples illustrated in FIGS. 2 and 4, the diaphragm pump is configured to cause a fluid to move from side A to side B of the diaphragm pump. In some examples, the diaphragm pump may cause a fluid pressure difference from side A to side B within channel 106, e.g., a higher pressure on side A and lower pressure on side B. In the example shown, channel 106 is configured to provide a fluid pathway from flexible tubes 104A-104F, e.g., inputs to channel 106, to the diaphragm pump, and continuing on from the diaphragm pump to flexible tubes 104G-104H, e.g., outputs from channel 106.

Figure 4:
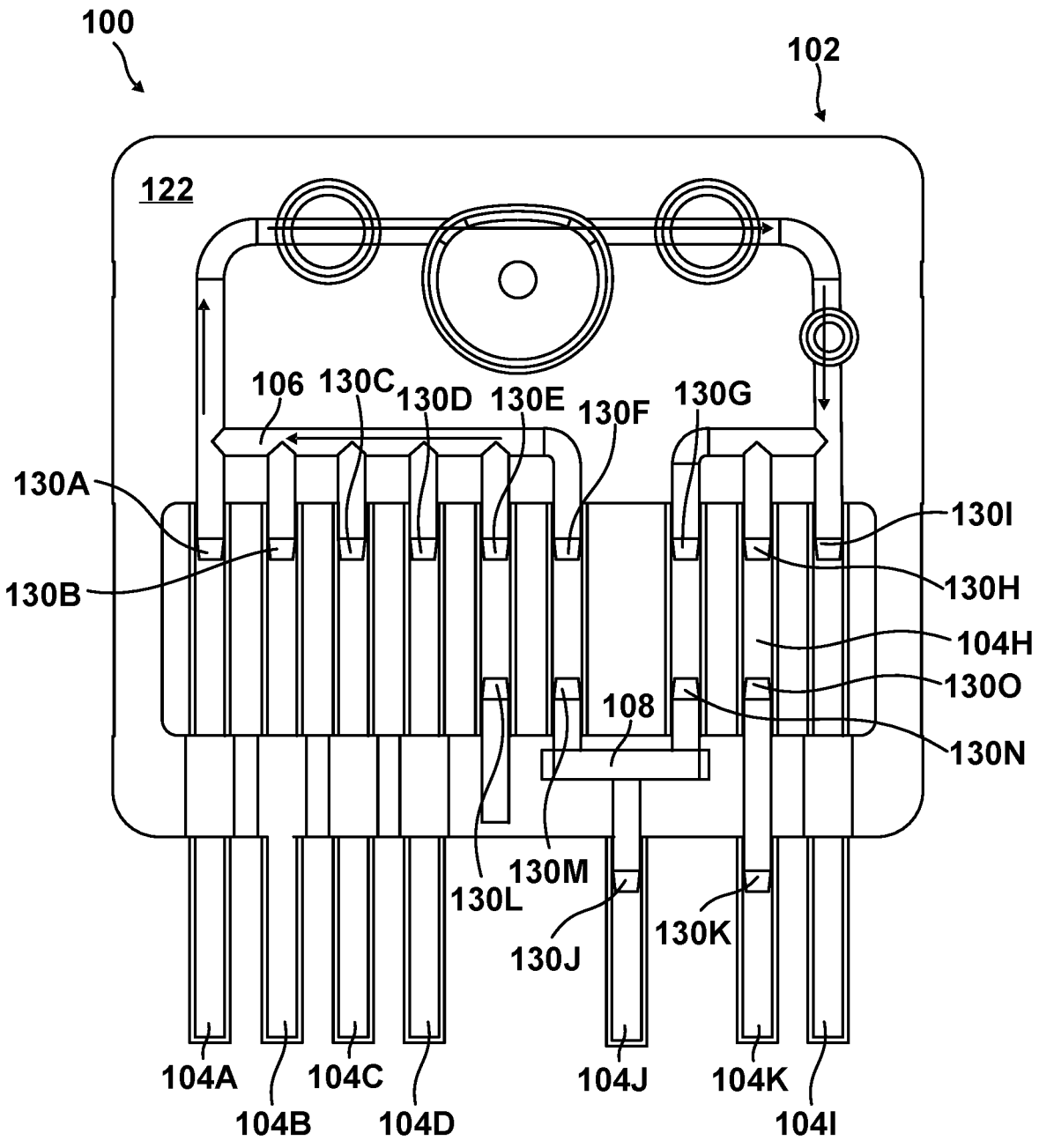
FIG. 4 is a view of a first side of the example PD cassette of FIG. 2.
Figure 5:
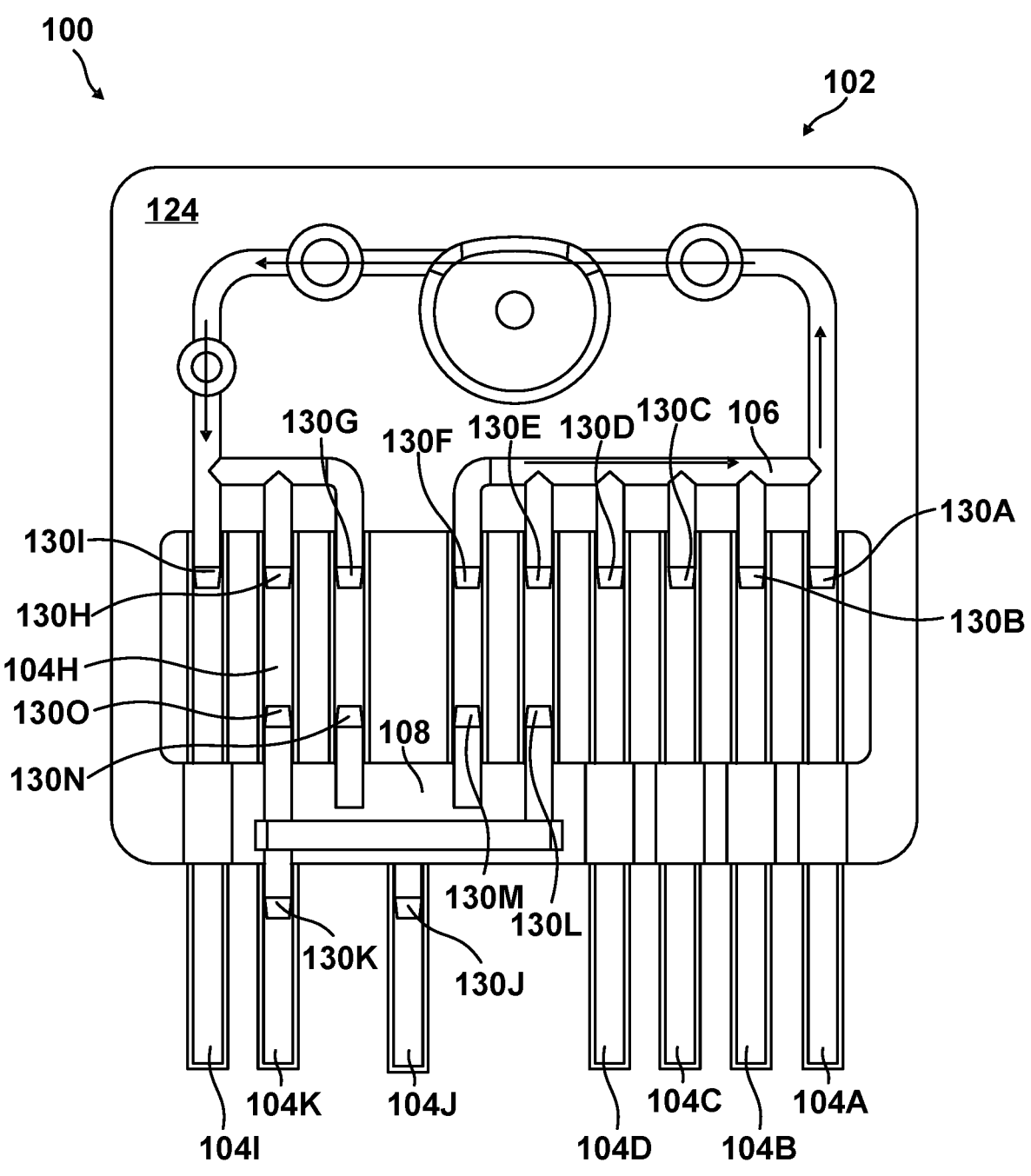
FIG. 5 is a view of a second side of the example PD cassette of FIG. 2.

FIGS. 4 and 5 illustrate first and second side views of cassette 100, e.g., "front" and "back" views. FIGS. 4 and 5 are described concurrently below.

FIG. 4 is a view of a first side of the example PD cassette 100 of FIG. 2. FIG. 5 is a view of a second side of the example PD cassette 100 of FIG. 2. In the examples shown, flexible tubes 104 are illustrated as partially transparent, e.g., to allow a view of example connectors 130A-1300, collectively or generally referred to as connectors 130. The view shown in FIG. 4 is of a major surface of first rigid member 122, and the view shown in FIG. 5 is of a major surface of second rigid member 124.

In the examples shown, each of flexible tubes 104 are configured to fluidically connect to a respective connector 130, e.g., via a friction and/or press fit, to fluidically connect to a fluid channel of rigid member 102. For example, a portion of the end of each flexible tube 104 can be configured to expand to receive a portion of a connector 130 within the lumen of the respective flexible tube 104. In other examples, a portion of each connector 130 may be configured to receive a portion of an end of a respective flexible tube 104, e.g., within one of channels 106-110. In some examples, flexible tubes 104 and connectors 130 are configured to fluidically connect via heat sealing, compression fittings, welding, soldering, or any combination thereof.

Figure 6:
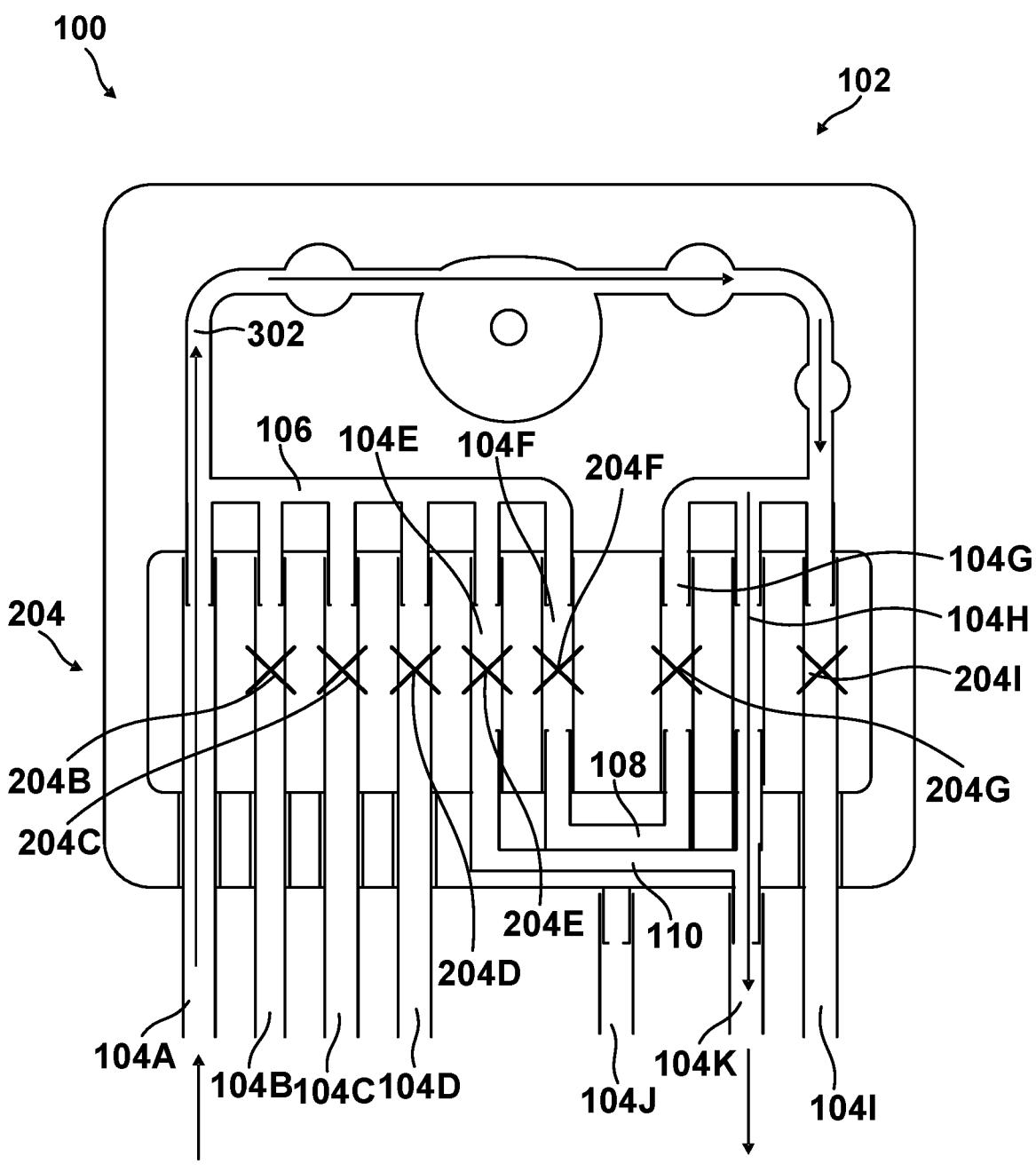
FIG. 6 is a view of a first side of an example cassette illustrating an example flow path through the cassette.

FIG. 6 is a side of a first side of the example PD cassette 100 of FIG. 2 illustrating an example fluid flow path 302 defined by the rigid member 102. In the example shown, flexible tubes 104 may be occluded by an external pressure applied at or near occlusion positions 204. The example shown illustrates occlusions positions 204A-204I (204A and 204H are unoccluded and are not visible in the example of FIG. 6, however, are illustrated in FIGS. 7A-7D or 8A-8C), collectively or generally referred to as occlusion positions 204. PD cycler 18 (FIG. 1) can include a plurality of actuators, e.g., actuators 132, configured to align with occlusions positions 204 to, under the control of control circuitry 30, selectively apply the pressure to tubes 104 at the respective occlusion position 204.

The example shown illustrates a first fluid flow path 302, e.g., which may be selected by control circuitry 30 and formed by occluding flexible tubes 104B-104G and 104I by applying an external pressure (e.g., compressing, pinching, etc.) to flexible tubes 104B-104G and 104I via actuators at occlusion positions 204B-204G and 204I. For example, cassette 100 may be placed in PD cycler 18 with one side of rigid member 102 adjacent to a rigid backing material, e.g., adjacent to first rigid member 122 or second rigid member 124, for a pin or extension of an actuator to press a flexible tube 104 against. In the example shown, flow of a fluid through flexible tubes 104B-104G and 104I is occluded (e.g., stopped, prevented, blocked) and flow of a fluid through flexible tubes 104A, 104H, and 104K is unoccluded (e.g., allowed, unblocked). The first fluid flow path 302 can be, for example, from a PD dialysate bag (e.g., a first input) fluidically connected to flexible tube 104A, through flexible tube 104A fluidically connected to channel 106 via connector 130A, through channel 106 to flexible tube 104H via connector 130H, and through flexible tubes 104H and 104K via connectors 1300 and 130K to a heater bag (e.g., a first output). In the example shown, the fluid may fill a portion of flexible tubes 104B-104G and 104I and channels 108 and 110, e.g., up to occlusion positions 204B-204G and 204I, but is stopped by the actuators from flowing past occlusion positions 204B-204G and 204I.

FIGS. 7A-7C and 8A-8C are views of the first side of the example PD cassette assembly 100 of FIG. 2 are substantially similar to FIG. 6 illustrated and described above, with each illustrating differing flow paths 304-314 between respective inputs and outputs, and are described concurrently below. In each of the examples shown, as with FIG. 6 described above, the examples show four inputs from four PD dialysate bags respectively fluidically connected to flexible tubes 104A-104D. Flexible tube 104I corresponds to an output to a waste or drain line fluidically connected to flexible tube 104I. Flexible tubes 104J and 104K correspond to I/O lines to a patient and a heater bag, respectively.

Figures 7A, 7B, 7C:
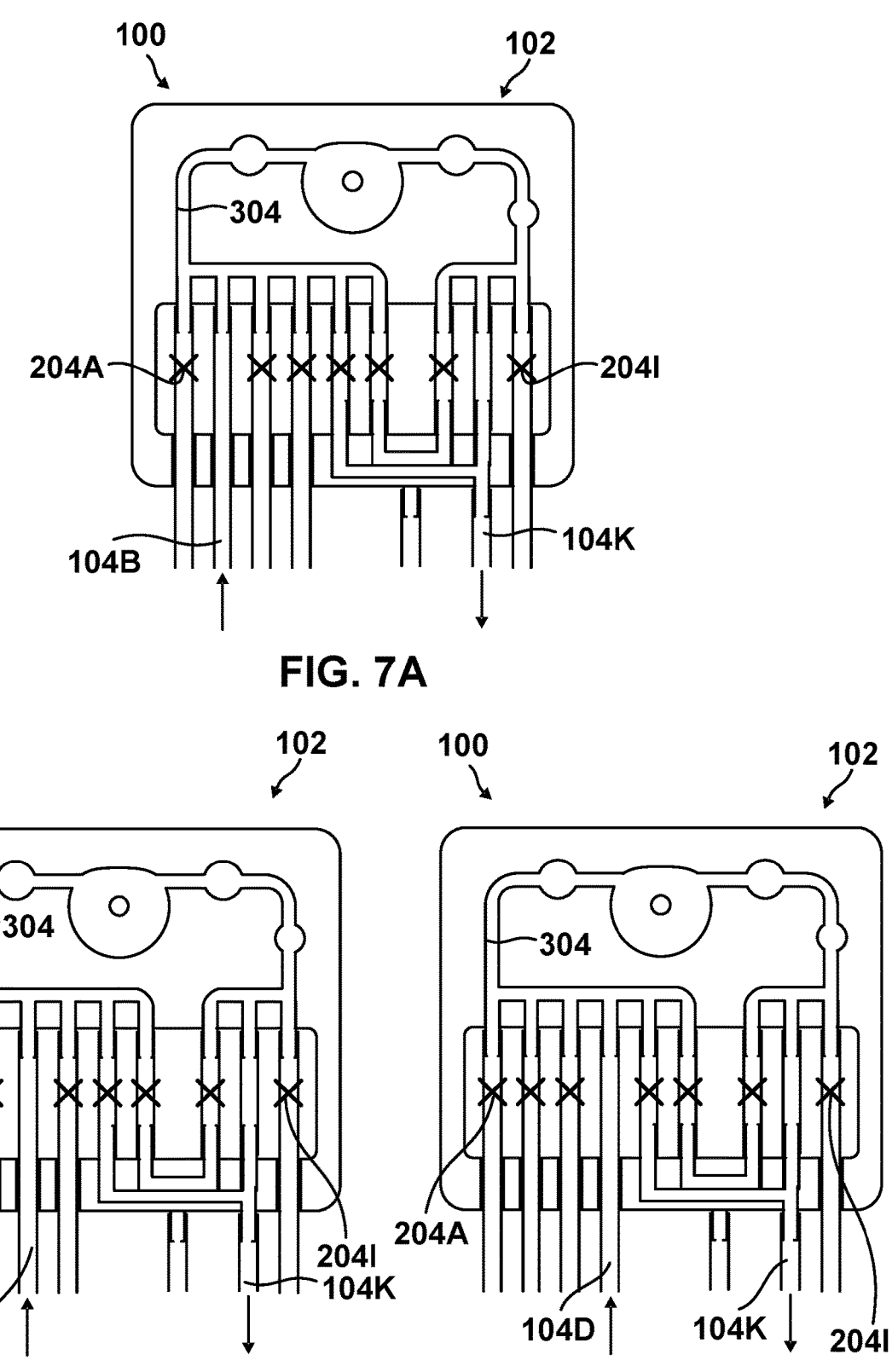
FIG. 7A is a view of a first side of an example cassette illustrating another example flow path through the cassette.
FIG. 7B is a view of a first side of an example cassette illustrating another example flow path through the cassette.
FIG. 7C is a view of a first side of an example cassette illustrating another example flow path through the cassette.

FIGS. 6 and FIGS. 7A-7C illustrate four fluid flow paths for providing PD dialysate to a heater bag in preparation for delivery to a patient, e.g., to warm the PD dialysate to at or near the body temperature of patient 12 so as to reduce discomfort of patient 12 upon delivery of the dialysate due to the temperature of the dialysate. FIG. 7A a side of a first side of cassette 100 illustrating a second example flow path 304 and is substantially similar to FIG. 6 illustrated and described above, except that flexible tube 104A is occluded and flexible tube 104B is unoccluded. FIG. 7B a side of a first side of cassette 100 illustrating a third example flow path 306 and is substantially similar to FIG. 6 illustrated and described above, except that flexible tube 104A is occluded and flexible tube 104C is unoccluded. FIG. 7C a side of a first side of cassette 100 illustrating a fourth example flow path 308 and is substantially similar to FIG. 6 illustrated and described above, except that flexible tube 104A is occluded and flexible tube 104D is unoccluded.

FIG. 8A a side of a first side of cassette 100 illustrating a fifth example flow path 310 and is substantially similar to FIG. 6 illustrated and described above, except that flexible tube 104A is occluded, flexible tube 104H is occluded, and flexible tubes 104E and 104I are unoccluded. Flow path 310 is from the heater bag via flexible tube 104K, through channel 110 to channel 106 via flexible tube 104E, and out to the drain line via flexible tube 104I, e.g., to remove excess dialysate from the heater bag such as after delivery to patient 12 or after a PD therapy session.

FIG. 8B a side of a first side of cassette 100 illustrating a sixth example fluid flow path 312 and is substantially similar to FIG. 6 illustrated and described above, except that flexible tube 104A is occluded, flexible tube 104H is occluded, and flexible tubes 104E and 104G are unoccluded. Fluid flow path 312 is from the heater bag via flexible tube 104K, through channel 110 to channel 106 via flexible tube 104E, through channel 106 to channel 108 via flexible tube 104G, and through channel 108 and out to patient 12 via flexible tube 104I, e.g., to provide PD dialysate from the heater bag to patient 12. In the example shown, a portion of channel 108 that includes connector 130I is not visible in order to more clearly illustrate channel 110.

FIG. 8C a side of a first side of cassette 100 illustrating a seventh example flow path 314 and is substantially similar to FIG. 6 illustrated and described above, except that flexible tube 104A is occluded, flexible tube 104H is occluded, and flexible tubes 104F and 104I are unoccluded. Flow path 314 is from patient 12 via flexible tube 104I, through channel 108 to channel 106 via flexible tube 104F, through channel 106 to the drain line via flexible tube 104I, e.g., to remove effluent from patient 12 to the drain line after a dwell time.

Figure 9:
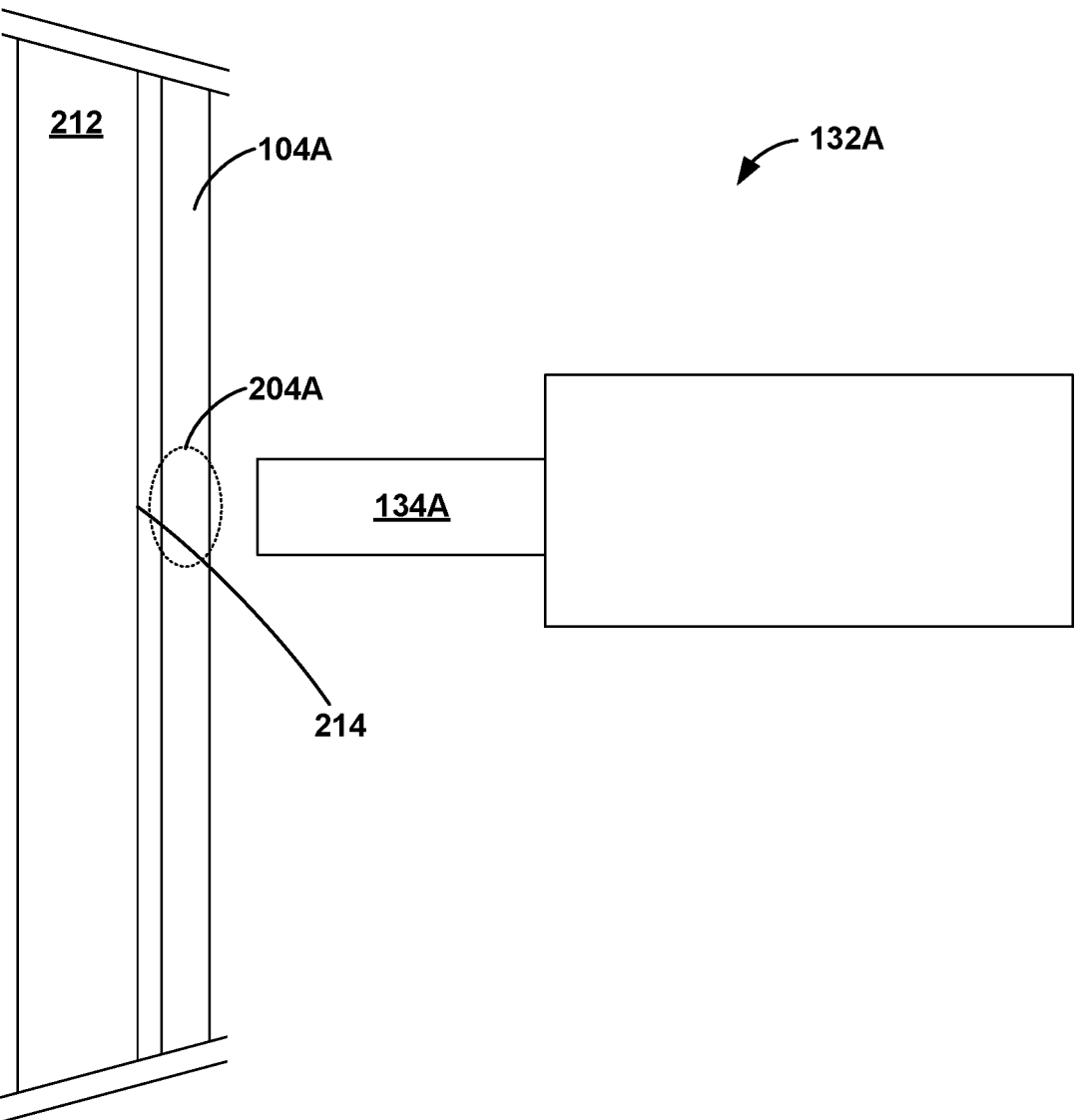
FIG. 9 is a side view of an example actuator and an example flexible tube in an unoccluded configuration.
Figure 10:
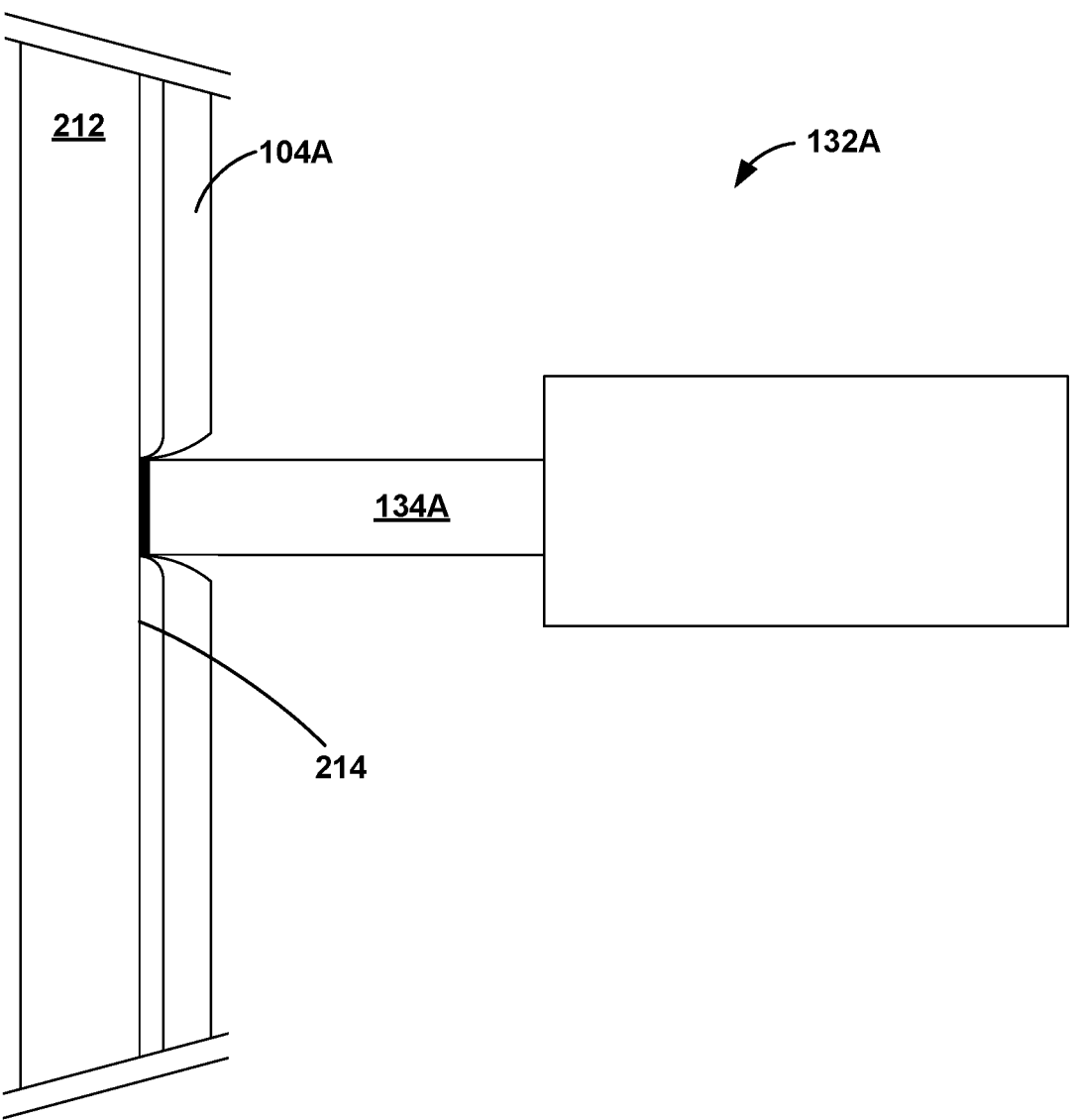
FIG. 10 is a side view of an example actuator and an example flexible tube in an occluded configuration.

FIG. 9 is a side view of an example actuator 132A and an example flexible tube 104A in an unoccluded configuration. FIG. 10 is a side view of an example actuator 132A and an example flexible tube 104A in an occluded configuration. FIGS. 9 and 10 are described concurrently below.

The example shown in FIG. 9 includes actuator 132A and flexible tube 104A. Actuator 132A may be positioned and held, e.g., mounted on a structure of PD cycler 18, such that pin 134A, when activated, applies a pressure to flexible tube 104A at occlusion position 204A. In some examples, PD cycler 18 may include backing 212, which may be positioned and held, e.g., mounted on a structure of PD cycler 18, such that pin 134A, when activated, may depress flexible tube 104A against a surface 214 of backing 212. Backing 212 may be any rigid structure configured to, in conjunction with actuator 132A, occlude flexible tube 104A. Actuator 132A may be configured to extend pin 134A to apply a pressure to depress, and occlude, flexible tube 104A, e.g., against surface 214 of backing 212. The example of FIG. 9 illustrates actuator 132A in an unactivated position and/or state, in which actuator 132A is configured to unocclude flexible tube 104A. For example, pin 134A is in an unextended position.

The example shown in FIG. 10 illustrates actuator 132A in an activated position and/or state, in which actuator 132A is occluding flexible tube 104A. For example, pin 134A is in an extended position.

Figure 11:
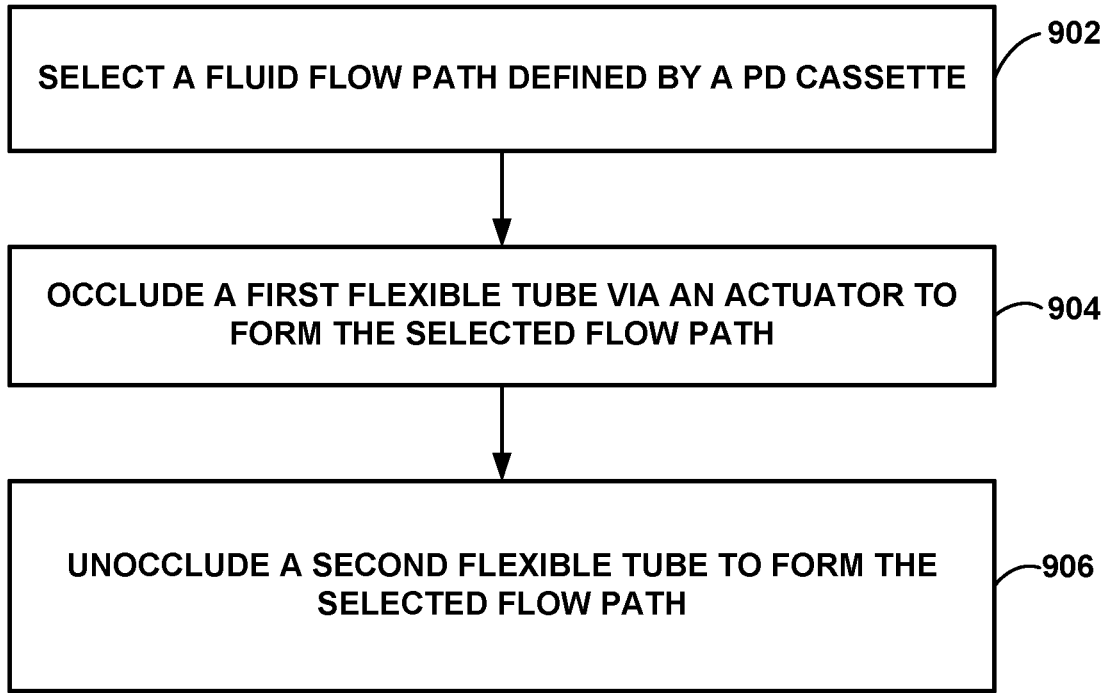
FIG. 11 is a flow diagram of an example method of forming a fluid flow paths through a PD cassette.

FIG. 11 is a flow diagram of an example method of forming a fluid flow paths via an example PD cassette 100. The example technique of FIG. 11 is described with respect to PD cycler 18 and control circuitry 30 of FIG. 1 and cassette 100 of FIGS. 2-8C. The example technique of FIG. 11 may be performed with any type of PD cycler 18 configured to selectively occlude flexible tubes 104.

Control circuitry 30 selects a fluid flow path of a plurality of fluid flow paths defined by a peritoneal dialysis cassette, e.g., cassette 100 (902). For example, control circuitry 30 may select a fluid flow path based on a stage of PD therapy to be delivered to patient 12, namely, to condition PD dialysate for delivery to patient 12, to deliver conditioned PD dialysate to patient 12, and to remove effluent from patient 12.

Control circuitry 30 causes one or more actuators to occlude one or more flexible tubes to form the selected flow path (904). For example, control circuitry 30 may cause an actuator to activate and occlude flexible tubes 104B-104G and 104I at occlusion positions 204B-204G and 204I to form fluid flow path 302 (FIG. 6) to deliver PD dialysate from a first PD dialysate bag to a heater bag for temperature conditioning. Control circuitry 30 may, in some cases, also cause different one or more actuators to unocclude a flexible tube to form the selected flow path (906). For example, if flexible tubes 104A and 104H were occluded, then control circuitry 30 may cause one or more actuators to deactivate and unocclude flexible tubes 104A and 104H to form fluid flow path 302 to deliver PD dialysate from a first PD dialysate bag to a heater bag for temperature conditioning.

Figure 12:
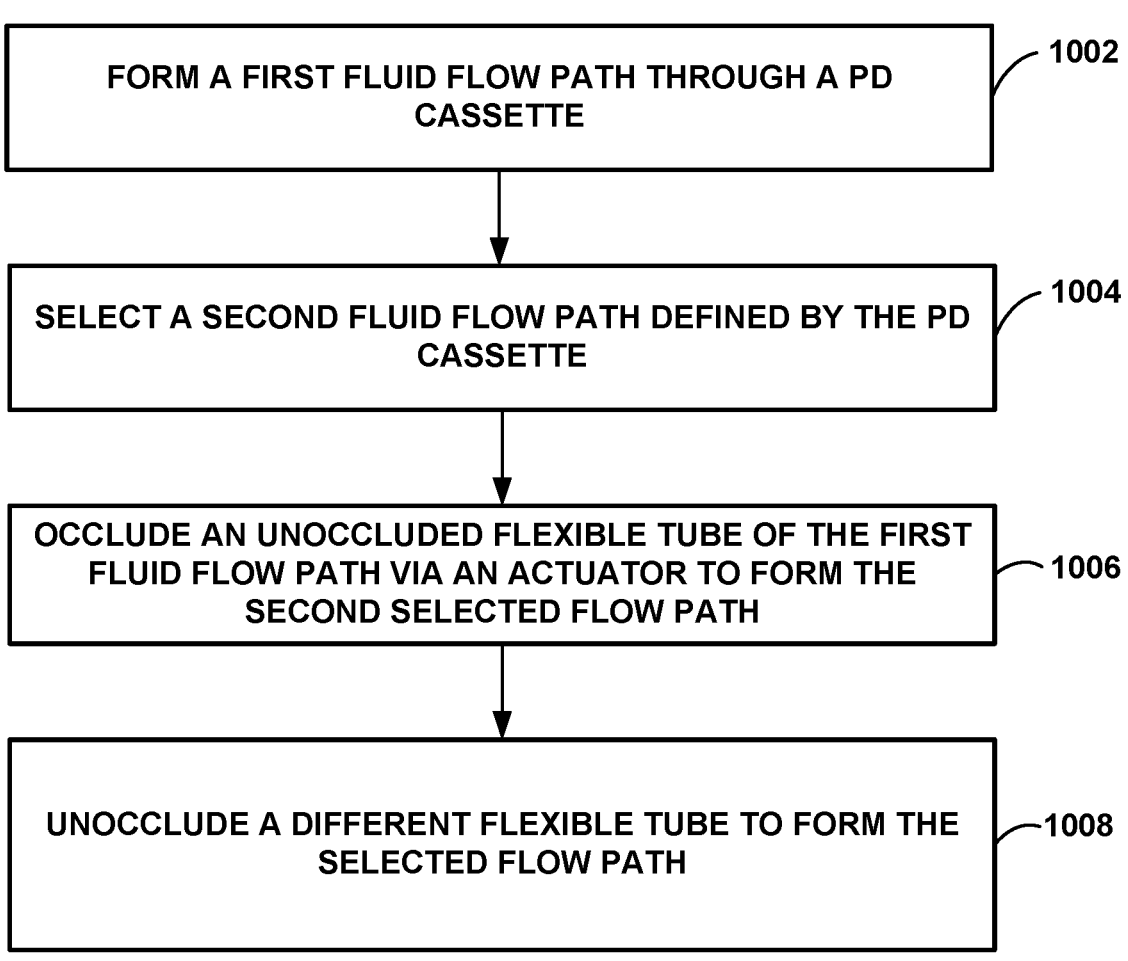
FIG. 12 is a flow diagram of an example method of changing from a first fluid flow path to a second different fluid flow path via an example PD cassette.

FIG. 12 is a flow diagram of an example method of changing from a first fluid flow path to a second different fluid flow path via an example PD cassette 100. The example technique of FIG. 12 is described with respect to PD cycler 18 and control circuitry 30 of FIG. 1 and cassette 100 of FIGS. 2-8C. The example technique of FIG. 12 may be performed with any type of PD cycler 18 configured to selectively occlude flexible tubes 104.

Control circuitry 30 controls one or more actuators to form a first fluid flow path through a PD cassette (1002). For example, control circuitry 30 may perform the method of FIG. 12 to form first fluid flow path 302 to deliver PD dialysate for conditioning.

After forming the first fluid flow path (1002), control circuitry 30 selects a second fluid flow path of a plurality of fluid flow paths defined by a peritoneal dialysis cassette, e.g., cassette 100 (1004). For example, control circuitry 30 may select second fluid flow path 312 (FIG. 8B) to deliver conditioned dialysate from the heater bag to patient 12.

Control circuitry 30 controls one or more actuators to occlude an unoccluded flexible tube to form the second selected flow path (1006). For example, control circuitry 30 may cause one or more actuators to activate and occlude flexible tubes 104A and 104H at occlusion positions 204A and 204H to form fluid flow path 312 to deliver PD dialysate from the heater bag to patient 12. In some examples, control circuitry 30 may also cause one or more actuators to release pressure applied to a different flexible tube to unocclude the different flexible tube to form the second selected flow path (1008). For example, control circuitry 30 may cause an actuator to deactivate and unocclude flexible tubes 104E and 104G to form fluid flow path 312 to deliver PD dialysate from the heater bag to patient 12.

The techniques described in this disclosure, including those attributed to PD cycler 18, control circuitry 30, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computerreadable medium such as RAM, ROM, NVRAM, EEPROM, FLASH memory, magnetic data storage media, optical data storage media, or the like. The instructions may be executed to support one or more aspects of the functionality described in this disclosure.

This disclosure includes the following non-limiting examples.

Example 1: An article includes a rigid member defining a plurality of fluid flow paths; and a plurality of flexible tubes each defining a lumen and configured to be occluded via a pressure applied externally to the respective lumen and unoccluded in the absence of the externally applied pressure, wherein each flexible tube is configured to be fluidically connected to a flow path of the plurality of flow paths, wherein different fluid flow paths of the plurality of fluid flow paths are defined by occluding different flexible tubes of the plurality of flexible tubes.

Example 2: The article of example 1, wherein each flexible tube of the plurality of flexible tubes is configured to be occluded via at least one of a mechanical, pneumatic, or mechanical and pneumatic actuator configured to collapse the lumen.

Example 3: The article of example 1 or 2, wherein the externally applied pressure is greater than or equal to 10 newtons (N) and less than or equal to 15N.

Example 4: The article of any one of examples 1 through 3, further comprising at least one of a temperature sensor or a pressure sensor configured to sense a temperature or a pressure, respectively, of fluid in at least one flow path of the plurality of flow paths.

Example 5: The article of any one of examples 1 through 4, wherein the rigid member comprises a first rigid member and a second rigid member connected together, each of the first and second rigid members defining a plurality of channels that form the plurality of fluid flow paths when the first and second rigid members are connected together.

Example 6: The article of example 5, wherein the first rigid member and the second rigid member are connected together via at least one of laser welding, ultrasonic welding, or hot plate welding.

Example 7: The article of any one of examples 1 through 6, wherein the rigid member further defines a plurality of fluidic connectors, each fluidic connector of the plurality of fluidic connectors being fluidically connected to a flow path of the plurality of fluid flow paths, wherein each flexible tube of the plurality of flexible tubes is configured to be connected to a respective fluidic connector by at least one of a friction fit or a heat seal.

Example 8: The article of any one of examples 1 through 7, wherein the plurality of fluid flow paths is less than or equal to ten fluid flow paths configured to selectively interconnect a plurality of external fluid connections, the plurality of external fluid connections comprising at least one patient fluid connection, at least one dialysate fluid connection, at least one drain fluid connection, and at least one fluid heating fluid connection.

Example 9: A system includes a cassette including a rigid member defining a plurality of fluid flow paths, each of the fluid flow paths including at least one fluidic connection to a fluid input or fluid output of the rigid member; and a plurality of flexible tubes each defining a lumen and configured to be occluded via a pressure applied externally to the lumen and unoccluded in the absence of the externally applied pressure, wherein each flexible tube is configured to be fluidically connected to a flow path of the plurality of fluid flow paths, wherein different fluid flow paths of the plurality of fluid flow paths are defined by occluding different flexible tubes of the plurality of flexible tubes; a peritoneal dialysis device comprising a plurality of actuators configured to apply the pressure externally to the plurality of flexible tubes; and control circuitry configured to selectively cause one or more actuators of the plurality of actuators to apply the pressure to or release the pressure from one or more flexible tubes of the plurality of flexible tubes.

Example 10: The system of example 9, further including a compressor configured to provide air to the plurality of actuators; and a pneumatic pump configured to move fluid through the plurality of fluid flow paths, wherein the plurality of actuators are pneumatic actuators, wherein the compressor is configured to provide less than 3000,000 Pascals (Pa) of pressure to the plurality of pneumatic actuators and the pneumatic pump.

Example 11: The system of example 9 or 10, wherein the plurality of actuators comprises at least one of a mechanical actuator, a pneumatic actuator, or a mechanical and pneumatic actuator.

Example 12: The system of any one of examples 9 through 11, wherein the cassette further comprises at least one of a temperature sensor or a pressure sensor configured to sense a temperature or a pressure, respectively, of fluid in at least one flow path of the plurality of flow paths.

Example 13: The system of any one of examples 9 through 12, wherein the rigid member comprises a first rigid member and a second rigid member connected together, each of the first and second rigid members defining a plurality of channels that form the plurality of fluid flow paths when the first and second rigid members are connected together.

Example 14: The system of example 13, wherein the first rigid member and the second rigid member are connected together via at least one of laser welding, ultrasonic welding, or hot plate welding.

Example 15: The system of any one of examples 9 through 14, wherein the rigid member further includes a first connector and a second connector configured to fluidically connect respective flexible tubes of the plurality of flexible tubes to the rigid member, wherein the flexible tubes are configured to mechanically connect to the first end connector and the second end connector by at least one of a friction fit or a heat seal.

Example 16: The system of any one of examples 9 through 15, wherein the plurality of fluid flow paths is less than or equal to ten fluid flow paths configured to selectively interconnect a plurality of external fluid connections, the plurality of external fluid connections comprising at least one patient fluid connection, at least one dialysate fluid connection, at least one drain fluid connection, and at least one fluid heating fluid connection.

Example 17: The system of any one of examples 9 through 16, wherein the control circuitry is configured to select and form one flow path of the plurality of flow paths via causing a first set of actuators of the plurality of actuators to occlude a corresponding first set of flexible tubes and causing a second set of actuators to unocclude a second set of flexible tubes, wherein the first set of actuators and the first set of flexible tubes are different from the second set of actuators and the second set of flexible tubes.

Example 18: A method includes selecting, via control circuitry, a fluid flow path of a plurality of fluid flow paths defined by a peritoneal dialysis cassette, the peritoneal dialysis cassette including a rigid member defining a plurality of fluid flow paths, each of the fluid flow paths including at least one fluidic connection to a fluid input or fluid output of the rigid member; and a plurality of flexible tubes each defining a lumen and configured to be occluded via a pressure applied externally to the respective tube and unoccluded in the absence of the externally applied pressure, wherein each flexible tube of the plurality of flexible tubes is configured to be fluidically connected to a flow path of the rigid member, wherein different fluid flow paths of the plurality of fluid flow paths are defined by occluding different flexible tubes of the plurality of flexible tubes; and causing, via the control circuitry, one or more actuators to occlude at least one flexible tube of the plurality of flexible tubes to define the fluid flow path.

Example 19: The method of example 18, wherein the one or more actuators is a first set of actuators and the at least one flexible tube comprises at least one first flexible tube, the method further comprising causing, via the control circuitry, at least one second actuator to unocclude a second flexible tube to define the fluid flow path.

Example 20: The method of example 19, wherein the fluid flow path is a first fluid flow path, the method further includes selecting, via the control circuitry, a second fluid flow path different from the first fluid flow path; and forming the second fluid flow path by at least: causing, via the control circuitry, the second actuator to occlude the second flexible tube; and causing, via the control circuitry, an actuator different from the second actuator to unocclude a flexible tube different from the second flexible tube.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

Based upon the above discussion and illustrations, it is recognized that various modifications and changes may be made to the disclosed technology in a manner that does not necessarily require strict adherence to the examples and applications illustrated and described herein. Such modifications do not depart from the true spirit and scope of various aspects of the disclosure, including aspects set forth in the claims.

Various examples have been described. These and other examples are within the scope of the following claims.

What is claimed is:

1. An article comprising:
a rigid member defining a plurality of fluid flow paths; and
a plurality of flexible tubes within the rigid member, each of the plurality of flexible tubes defining a lumen and configured to be occluded via a pressure applied externally to at least a portion of the lumen of a respective flexible tube of the plurality of flexible tubes within the rigid member and unoccluded in an absence of the externally applied pressure,
wherein each flexible tube of the plurality of flexible tubes is configured to be fluidically connected within the rigid member to a fluid flow path of the plurality of fluid flow paths,
wherein different fluid flow paths of the plurality of fluid flow paths are defined by occluding different flexible tubes of the plurality of flexible tubes.

2. The article of claim 1, wherein each flexible tube of the plurality of flexible tubes is configured to be occluded via at least one of a mechanical actuator, a pneumatic actuator, or a mechanical and pneumatic actuator configured to collapse the lumen.

3. The article of claim 1, wherein the externally applied pressure is greater than or equal to 10 newtons (N) and less than or equal to 15N.

4. The article of claim 1, further comprising at least one of a temperature sensor or a pressure sensor configured to sense a temperature or a pressure, respectively, of fluid in at least one fluid flow path of the plurality of fluid flow paths.

5. The article of claim 1, wherein the rigid member comprises a first rigid member and a second rigid member connected together, each of the first rigid member and the second rigid member defining a plurality of channels that form the plurality of fluid flow paths when the first rigid member and the second rigid member are connected together.

6. The article of claim 5, wherein the first rigid member and the second rigid member are connected together via at least one of laser welding, ultrasonic welding, or hot plate welding.

7. The article of claim 1, wherein the rigid member further defines a plurality of fluidic connectors, each fluidic connector of the plurality of fluidic connectors being fluidically connected to a fluid flow path of the plurality of fluid flow paths, wherein each flexible tube of the plurality of flexible tubes is configured to be connected to a respective fluidic connector of the plurality of fluidic connectors by at least one of a friction fit or a heat seal.

8. The article of claim 1, wherein the plurality of fluid flow paths is less than or equal to ten fluid flow paths configured to selectively interconnect a plurality of external fluid connections, the plurality of external fluid connections comprising at least one patient fluid connection, at least one dialysate fluid connection, at least one drain fluid connection, and at least one fluid heating fluid connection.

9. A system comprising:
a cassette comprising:
a rigid member defining a plurality of fluid flow paths, each of the plurality of fluid flow paths including at least one fluidic connection to a fluid input or a fluid output of the rigid member; and
a plurality of flexible tubes within the rigid member, each of the plurality of flexible tubes defining a lumen and configured to be occluded via a pressure applied externally to at least a portion of the lumen of a respective flexible tube of the plurality of flexible tubes within the rigid member and unoccluded in an absence of the externally applied pressure,
wherein each flexible tube of the plurality of flexible tubes is configured to be fluidically connected to a fluid flow path of the plurality of fluid flow paths,
wherein different fluid flow paths of the plurality of fluid flow paths are defined by occluding different flexible tubes of the plurality of flexible tubes;
a peritoneal dialysis device comprising a plurality of actuators configured to apply the pressure externally to the plurality of flexible tubes; and
control circuitry configured to selectively cause one or more actuators of the plurality of actuators to apply the pressure to or release the pressure from one or more flexible tubes of the plurality of flexible tubes.

10. The system of claim 9, further comprising:
a compressor configured to provide air to the plurality of actuators; and
a pneumatic pump configured to move fluid through the plurality of fluid flow paths,
wherein the plurality of actuators are pneumatic actuators,
wherein the compressor is configured to provide less than 3,000,000 Pascals (Pa) of pressure to the pneumatic actuators and the pneumatic pump.

11. The system of claim 9, wherein the plurality of actuators comprises at least one of a mechanical actuator, a pneumatic actuator, or a mechanical and pneumatic actuator.

12. The system of claim 9, wherein the cassette further comprises at least one of a temperature sensor or a pressure sensor configured to sense a temperature or a pressure, respectively, of fluid in at least one fluid flow path of the plurality of fluid flow paths.

13. The system of claim 9, wherein the rigid member comprises a first rigid member and a second rigid member connected together, each of the first rigid member and the second rigid member defining a plurality of channels that form the plurality of fluid flow paths when the first rigid member and the second rigid member are connected together.

14. The system of claim 13, wherein the first rigid member and the second rigid member are connected together via at least one of laser welding, ultrasonic welding, or hot plate welding.

15. The system of claim 9, wherein the rigid member further includes a first connector and a second connector configured to fluidically connect respective flexible tubes of the plurality of flexible tubes to the rigid member, wherein the respective flexible tubes are configured to mechanically connect to the first connector and the second connector by at least one of a friction fit or a heat seal.

16. The system of claim 9, wherein the plurality of fluid flow paths is less than or equal to ten fluid flow paths configured to selectively interconnect a plurality of external fluid connections, the plurality of external fluid connections comprising at least one patient fluid connection, at least one dialysate fluid connection, at least one drain fluid connection, and at least one fluid heating fluid connection.

17. The system of claim 9, wherein the control circuitry is configured to select and form one fluid flow path of the plurality of fluid flow paths via causing a first set of actuators of the plurality of actuators to occlude a corresponding first set of flexible tubes of the plurality of flexible tubes and causing a second set of actuators of the plurality of actuators to unocclude a second set of flexible tubes of the plurality of flexible tubes, wherein the first set of actuators and the first set of flexible tubes are different from the second set of actuators and the second set of flexible tubes.

18. A method comprising:

selecting, via control circuitry, a fluid flow path of a plurality of fluid flow paths defined by a peritoneal dialysis cassette, the peritoneal dialysis cassette comprising:

a rigid member defining the plurality of fluid flow paths, each fluid flow path of the plurality of fluid flow paths including at least one fluidic connection to a fluid input or a fluid output of the rigid member; and a plurality of flexible tubes within the rigid member, each of the plurality of flexible tubes defining a lumen and configured to be occluded via a pressure applied externally to at least a portion of the lumen of a respective flexible tube of the plurality of flexible tubes and unoccluded in an absence of the externally applied pressure, wherein each flexible tube of the plurality of flexible tubes is configured to be fluidically connected to a fluid flow path of the plurality of fluid flow paths of the rigid member, wherein different fluid flow paths of the plurality of fluid flow paths are defined by occluding different flexible tubes of the plurality of flexible tubes; and causing, via the control circuitry, one or more actuators to occlude at least one flexible tube of the plurality of flexible tubes to define the fluid flow path.

19. The method of claim 18, wherein the one or more actuators is a first set of actuators and the at least one flexible tube comprises a first flexible tube, the method further comprising causing, via the control circuitry, at least one second actuator of the one or more actuators to unocclude a second flexible tube of the plurality of flexible tubes to define the fluid flow path.

20. The method of claim 19, wherein the fluid flow path is a first fluid flow path, the method further comprising:

selecting, via the control circuitry, a second fluid flow path of the plurality of fluid flow paths different from the first fluid flow path; and forming the second fluid flow path by at least:

causing, via the control circuitry, the at least one second actuator to occlude the second flexible tube; and causing, via the control circuitry, an actuator of the one or more actuators different from the second actuator to unocclude a flexible tube of the plurality of flexible tubes different from the second flexible tube.

\* \* \* \* \*